(12) United States Patent
Errico et al.

(10) Patent No.: US 7,811,289 B2
(45) Date of Patent: Oct. 12, 2010

(54) ARTIFICIAL INTERVERTEBRAL DISC TRIAL HAVING A CONTROLLABLY SEPARABLE DISTAL END

(75) Inventors: Joseph P. Errico, Green Brook, NJ (US); Michael W. Dudasik, Nutley, NJ (US); Rafail Zubok, Midland Park, NJ (US)

(73) Assignee: SpineCore, Inc., Summit, NJ (US)

( * ) Notice: Subject to any disclaimer, the term of this patent is extended or adjusted under 35 U.S.C. 154(b) by 973 days.

(21) Appl. No.: 10/784,646

(22) Filed: Feb. 23, 2004

(65) Prior Publication Data

US 2004/0167537 A1    Aug. 26, 2004

Related U.S. Application Data

(63) Continuation of application No. 10/282,356, filed on Oct. 29, 2002, now Pat. No. 7,169,182, which is a continuation-in-part of application No. 10/256,160, filed on Sep. 26, 2002, now Pat. No. 6,989,032, which is a continuation-in-part of application No. 10/175,417, filed on Jun. 19, 2002, now Pat. No. 7,563,285, which is a continuation-in-part of application No. 10/151,280, filed on May 20, 2002, now Pat. No. 7,604,664, which is a continuation-in-part of application No. 09/970,479, filed on Oct. 4, 2001, now Pat. No. 6,669,730, and a continuation-in-part of application No. 10/140,153, filed on May 7, 2002, now abandoned, which is a continuation-in-part of application No. 09/970,479, filed on Oct. 4, 2001, now Pat. No. 6,669,730, which is a continuation-in-part of application No. 09/968,046, filed on Oct. 1, 2001, now abandoned, said application No. 10/140,153 is a continuation-in-part of application No. 10/128,619, filed on Apr. 23, 2002, now Pat. No. 6,863,689, and a continuation-in-part of application No. 09/982,148, filed on Oct. 18, 2001, now Pat. No. 6,673,113, which is a continuation-in-part of application No. 09/906,119, filed on Jul. 16, 2001, now Pat. No. 6,607,559.

(51) Int. Cl.
A61B 17/56 (2006.01)
(52) U.S. Cl. .......................................... 606/90; 606/99
(58) Field of Classification Search .............. 623/17.14, 623/17.15, 17.16; 606/99, 102, 61, 86 A, 606/246, 914, 90, 105, 57, 282; 81/3.57, 81/94, 106, 136, 408; 254/26 E, 27
See application file for complete search history.

(56) References Cited

U.S. PATENT DOCUMENTS 1,882,462 A    10/1932    Weber (Continued)

FOREIGN PATENT DOCUMENTS

| EP | 0369603 A1 | 5/1990 |
|----|------------|--------|
| WO | 9929271 A1 | 6/1999 |
| WO | WO02071986 A2 * | 9/2002 |

OTHER PUBLICATIONS

Surgical Technique Using FRA Spacer Instruments, Technique Guide, Synthes Spine, 1998.

*Primary Examiner*—Brian E. Pellegrino
(74) *Attorney, Agent, or Firm*—Lerner, David, Littenberg, Krumholz & Mentlik, LLP

(57) ABSTRACT

Instrumentation for implanting an artificial intervertebral disc includes a dynamic trial for distracting an intervertebral space and/or determining the appropriate size of disc to be implanted, which dynamic trial includes a shaft, at least two distal extensions coupled to the shaft, a bifurcated trial having a first trial half of the bifurcated trial coupled to a first of the extensions and having a second trial half of the bifurcated trial coupled to a second of the extensions, and a pin located between the extensions, wherein movement of the pin in a distal direction increases a separation between the extensions, and wherein varying the separation between the extensions varies a separation between the trial halves.

19 Claims, 18 Drawing Sheets

U.S. PATENT DOCUMENTS

| | | | |
|---|---|---|---|
| 4,566,466 A * | 1/1986 | Ripple et al. | 606/102 |
| 5,015,247 A | 5/1991 | Michelson | |
| 5,306,309 A | 4/1994 | Wagner et al. | |
| 5,314,477 A * | 5/1994 | Marnay | 623/17.15 |
| 5,370,697 A * | 12/1994 | Baumgartner | 623/17.15 |
| 5,667,347 A | 9/1997 | Matthews | |
| 6,159,211 A | 12/2000 | Boriani et al. | |
| 6,174,311 B1 | 1/2001 | Branch et al. | |
| 6,319,257 B1 | 11/2001 | Carignan et al. | |
| 6,478,800 B1 * | 11/2002 | Fraser et al. | 606/99 |
| 6,652,533 B2 | 11/2003 | O'Neil | |
| 6,723,127 B2 | 4/2004 | Ralph et al. | |
| 6,755,841 B2 | 6/2004 | Fraser et al. | |
| 7,070,598 B2 | 7/2006 | Lim et al. | |
| 7,087,055 B2 | 8/2006 | Lim et al. | |
| 7,118,580 B1 | 10/2006 | Beyersdorff et al. | |
| 7,122,055 B2 | 10/2006 | Ralph et al. | |
| 7,153,325 B2 | 12/2006 | Kim et al. | |
| 2002/0116009 A1 | 8/2002 | Fraser et al. | |
| 2002/0161375 A1 | 10/2002 | Ralph et al. | |
| 2003/0055503 A1 | 3/2003 | O'Neil | |
| 2003/0176925 A1 * | 9/2003 | Paponneau | 623/17.16 |
| 2003/0195514 A1 | 10/2003 | Trieu et al. | |
| 2003/0233097 A1 | 12/2003 | Ferree | |
| 2003/0233145 A1 | 12/2003 | Landry et al. | |
| 2003/0233148 A1 | 12/2003 | Ferree | |
| 2004/0030387 A1 | 2/2004 | Landry et al. | |
| 2004/0030390 A1 | 2/2004 | Ferree | |
| 2004/0143332 A1 | 7/2004 | Krueger et al. | |
| 2004/0148027 A1 * | 7/2004 | Errico et al. | 623/17.16 |
| 2004/0158325 A1 * | 8/2004 | Errico et al. | 623/17.11 |
| 2004/0204762 A1 | 10/2004 | Ralph et al. | |
| 2004/0220582 A1 | 11/2004 | Keller | |
| 2005/0119665 A1 | 6/2005 | Keller | |
| 2005/0182416 A1 | 8/2005 | Lim et al. | |
| 2006/0064107 A1 | 3/2006 | Bertagnoli et al. | |
| 2007/0239162 A1 | 10/2007 | Bhatnagar et al. | |

* cited by examiner (Section A-A of Fig. 1a)

(Section B-B of Fig. 1a)

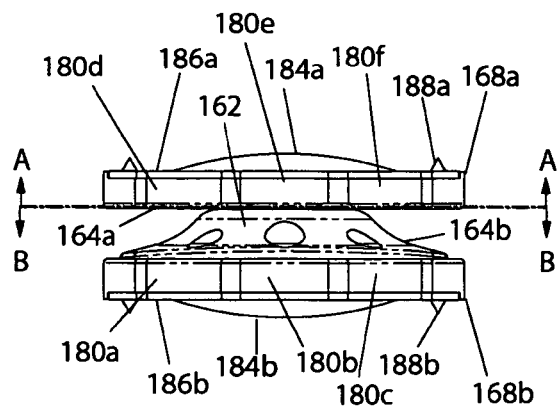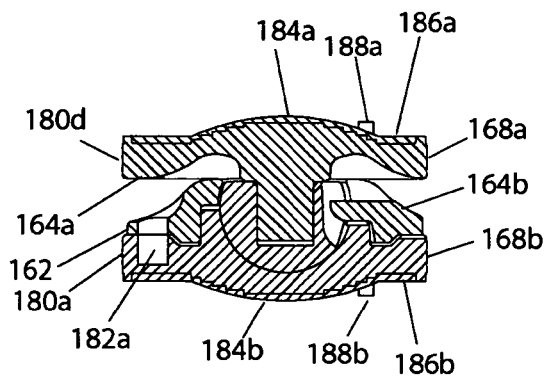
FIG. 1g
FIG. 1h
(Section C-C on Fig. 1i)
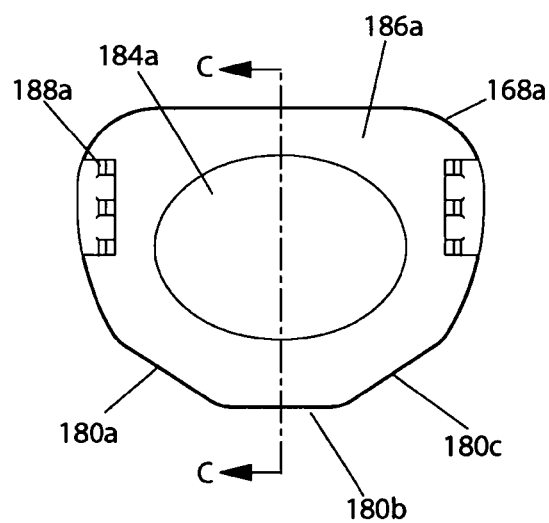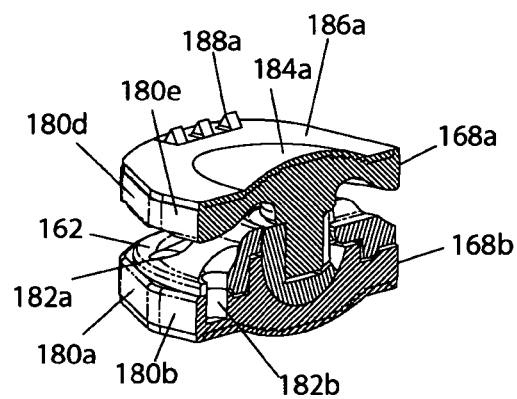
FIG. 1i
FIG. 1j
(Perspective of Fig. 1h)

(Section A-A on Fig. 1g)

(Section B-B on Fig. 1g)

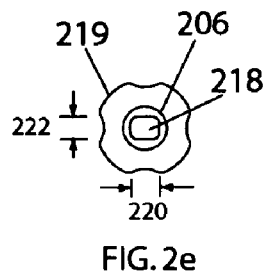
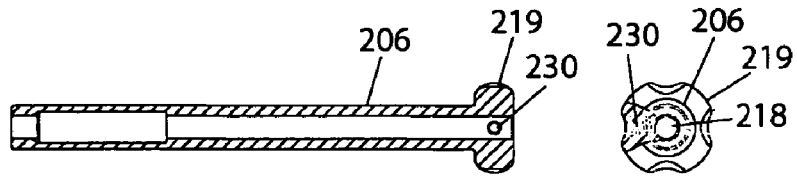
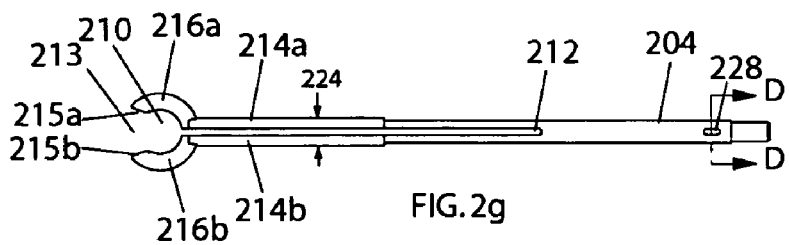
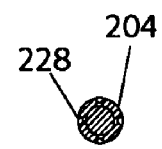
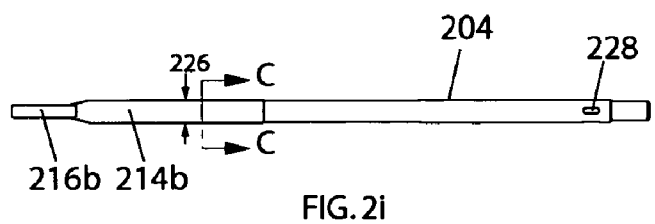
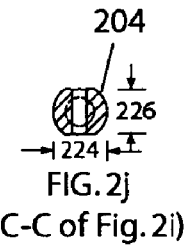
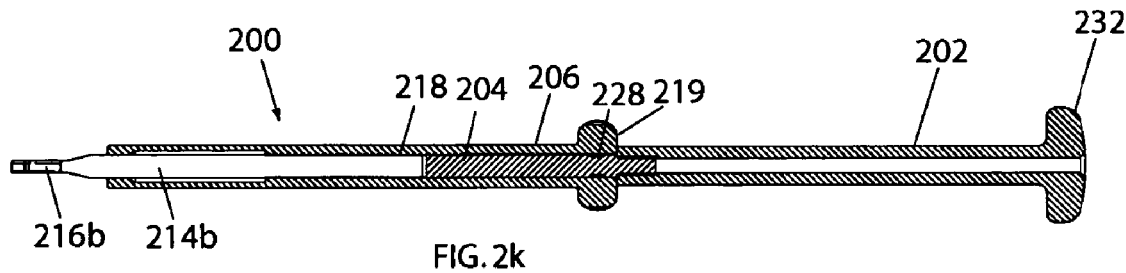

(Section A-A of Fig. 3b)

(Section A-A of Fig. 4b)

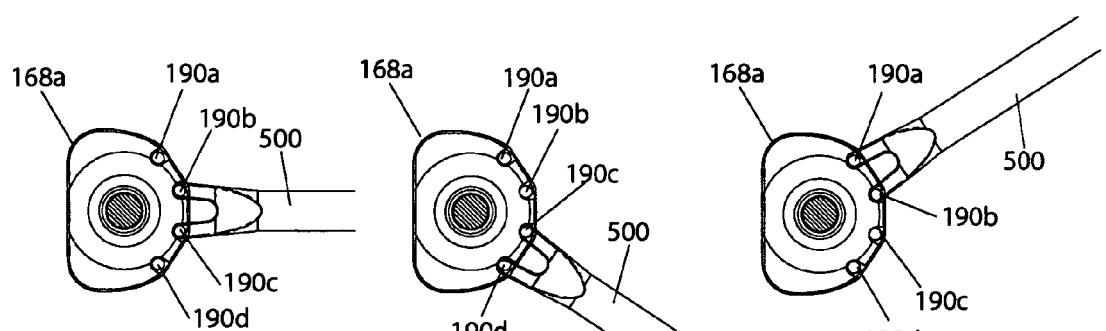
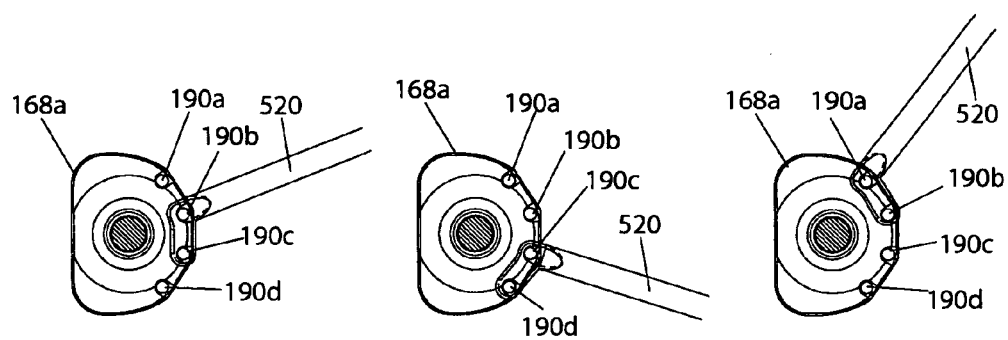
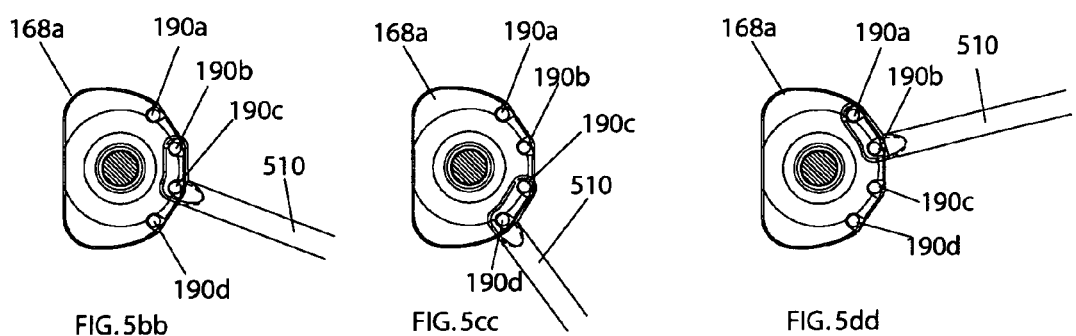

ARTIFICIAL INTERVERTEBRAL DISC TRIAL HAVING A CONTROLLABLY SEPARABLE DISTAL END

CROSS-REFERENCE TO RELATED APPLICATIONS

The present application is a continuation of U.S. patent application Ser. No. 10/282,356 (filed Oct. 29, 2002), now U.S. Pat. No. 7,169,182, which is a continuation-in-part application of U.S. patent application Ser. No. 10/256,160 (filed Sep. 26, 2002), now U.S. Pat. No. 6,989,032, which is a continuation-in-part application of U.S. patent application Ser. No. 10/175,417 (filed Jun. 19, 2002), now U.S. Pat. No. 7,563,285 which is a continuation-in-part application of U.S. patent application Ser. No. 10/151,280 (filed May 20, 2002), now U.S. Pat. No. 7,604,664 which is a continuation-in-part application of both U.S. patent application Ser. No. 09/970,479 (filed Oct. 4, 2001), now U.S. Pat. No. 6,669,730 as well as U.S. patent application Ser. No. 10/140,153 (filed May 7, 2002), now abandoned with application Ser. No. 09/970,479 being a continuation-in-part application of U.S. patent application Ser. No. 09/968,046 (filed Oct. 1, 2001), now abandoned and application Ser. No. 10/140,153 being a continuation-in-part application of both, the U.S. Pat. No. 6,669,730 (detailed above) as well as U.S. patent application Ser. No. 10/128,619 (filed Apr. 23, 2002), now U.S. Pat. No. 6,863,689, which is a continuation-in-part application of both U.S. patent application Ser. No. 09/906,119 (filed Jul. 16, 2001), now U.S. Pat. No. 6,607,559 as well as U.S. patent application Ser. No. 09/982,148 (filed Oct. 18, 2001), now U.S. Pat. No. 6,673,113. All of the above mentioned applications are hereby incorporated by reference herein in their respective entireties.

FIELD OF THE INVENTION

This invention relates generally to systems and methods for use in spine arthroplasty, and more specifically to instruments for distracting an intervertebral space, inserting and removing trial artificial intervertebral discs, and inserting, impacting, repositioning, leveling and extracting artificial intervertebral discs, and methods of use thereof.

BACKGROUND OF THE INVENTION

The bones and connective tissue of an adult human spinal column consists of more than twenty discrete bones coupled sequentially to one another by a tri-joint complex that consists of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. With respect to the failure of the intervertebral disc, and the insertion of implants and/or height restorative devices, several methods and devices have been disclosed in the prior art that achieve immobilization and/or fusion of adjacent bones by implanting artificial assemblies in or on the spinal column. More recently, the development of non-fusion implant devices, which purport to permit continued natural movement in the tri-joint complex, have provided great promise as a preferably alternative to fusion devices. The region of the back that needs to be corrected, as well as the individual variations in anatomy, determine the appropriate surgical protocol and implantation assembly. Generally, the preparation of the intervertebral space for the receipt of fusion or non-fusion devices involves removing the damaged disc material and thereafter distracting the adjacent vertebral bones to their appropriate distance apart. Once the proper height of the intervertebral space is restored, the fusion or non-fusion device can be implanted.

It is an object of the invention to provide instrumentation and methods that enable surgeons to more accurately, easily, and efficiently prepare the intervertebral space and implant fusion or non-fusion devices. Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which includes static trial artificial intervertebral discs (sometimes referred to herein as a "static trial"), a static trial artificial intervertebral disc holder (sometimes referred to herein as a "static trial holder"), a dynamic trial artificial intervertebral disc (sometimes referred to herein as a "dynamic trial"), an artificial intervertebral disc inserter/impactor (sometimes referred to herein as an "inserter/impactor"), an artificial intervertebral disc repositioner/extractor (sometimes referred to herein as a "repositioner/extractor"), and an artificial intervertebral disc leveler (sometimes referred to herein as a "leveler").

More particularly, the systems and methods disclosed herein are intended for use in spine arthroplasty procedures, and specifically for use with the systems and methods described herein in conjunction with the systems and method described in U.S. patent application Ser. No. 10/256,160 (filed Sep. 26, 2002) entitled "Artificial Intervertebral Disc Having Limited Rotation Using a Captured Ball and Socket Joint With a Solid Ball and Compression Locking Post" (hereinafter referred to as "the '160 application") as well as U.S. patent application Ser. No. 09/906,127 (filed Jul. 16, 2001) entitled "Insertion Tool For Use With Intervertebral Spacers" (hereinafter referred to as "the '127 application"), both applications of which are mentioned above. However, it should be understood that the systems and methods described herein are also suitable for use with other systems and methods without departing from the scope of the invention.

For example, while the static trials described herein are primarily intended for use in determining the appropriate size of particular embodiments of the artificial intervertebral disc implants described in the '160 application to be implanted (or whether a particular size can be implanted) into the distracted intervertebral space, they can also be used for determining the appropriate size of any other suitably configured orthopedic implant or trial to be implanted (or whether a particular size can be implanted) into the distracted intervertebral space.

And, for example, while the static trial holder described herein is primarily intended for use in holding, inserting, removing, and otherwise manipulating the static trials described herein, it can also be used for manipulating any embodiment of the trial spacers described in the '127 application (also referred to therein and herein as distraction spacers), and can also be used for manipulating any other suitably configured orthopedic device.

And, for example, while the dynamic trial described herein is primarily intended for use in distracting an intervertebral space according to the procedures described herein and/or for determining the appropriate size of particular embodiments artificial intervertebral disc implants described in the '160 application to be implanted (or whether a particular size can be implanted) into the distracted intervertebral space, it can also be used for distracting an intervertebral space according to other procedures and/or for determining the appropriate size of any other suitably configured orthopedic implant or trial to be implanted (or whether a particular size can be implanted) into the distracted intervertebral space.

And, for example, while the inserter/impactor described herein is primarily intended for use in holding, inserting, removing, impacting, extracting, and otherwise manipulating particular embodiments of the artificial intervertebral disc implants described in the '160 application, it can also be used for manipulating any other suitably configured orthopedic implant or trial.

And, for example, while the repositioners/extractors described herein is primarily intended for use in repositioning and/or extracting and/or otherwise manipulating particular embodiments of the artificial intervertebral disc implants described in the '160 application, it can also be used for manipulating any other suitably configured orthopedic implant or trial.

And, for example, while the leveler described herein is primarily intended for use in setting the proper position of, and/or otherwise manipulating, particular embodiments of the artificial intervertebral disc implants described in the '160 application, it can also be used for manipulating any other suitably configured orthopedic implant or trial.

While the instrumentation described herein (e.g., the static trials, static trial holder, dynamic trial, inserter/impactor, repositioners/extractors, and leveler) will be discussed for use with the artificial intervertebral disc of FIGS. 1g-n, such discussions are merely by way of example and not intended to be limiting of their uses. Thus, it should be understood that the tools can be used with any of the artificial intervertebral discs disclosed in the '160 application, or any other artificial intervertebral disc having (or being modifiable or modified to have) suitable features therefor. Moreover, it is anticipated that the features of the artificial intervertebral disc (e.g., the flat surfaces and accompanying holes) and/or the static trials (e.g., the cylindrical trunks and flat surfaces and accompanying holes) that are used by the tools discussed herein to hold and/or manipulate these devices (such features, it should be noted, were first shown and disclosed in the '160 application and the '127 application) can be applied, individually or collectively or in various combinations, to other trials, spacers, artificial intervertebral discs or other orthopedic devices as stand-alone innovative features for enabling such trials, spacers, artificial intervertebral discs, or other orthopedic devices to be more efficiently and more effectively held and/or manipulated by the tools described herein or by other tools having suitable features. In addition, it should be understood that the invention encompasses artificial intervertebral discs, spacers, trials (static or dynamic), and/or other orthopedic devices, that have one or more of the features disclosed herein, in any combination, and that the invention is therefore not limited to artificial intervertebral discs, spacers, trials, and/or other orthopedic devices having all of the features simultaneously.

More particularly with regard to the static trials described herein, a plurality of static trials are provided primarily for use in determining the appropriate size of an artificial intervertebral disc to be implanted (or whether a particular size of the artificial intervertebral disc can be implanted) into the distracted intervertebral space (e.g., the artificial intervertebral disc 160 of FIGS. 1*g-n*). Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. Accordingly, preferably, each of the plurality of static trials 100 for use with a particular plurality of differently sized artificial intervertebral discs would have a respective width and depth dimension set corresponding to the width and depth of a respective one of the plurality of differently sized artificial intervertebral discs. For example, the plurality of static trials 100 for use with the set of artificial intervertebral discs described for example could include static trials 100 having widths being either 35 mm or 40 mm, and depths ranging from 14 mm to 18 mm in 1 mm increments, for a total of 10 static trials. It should be understood that the artificial intervertebral discs and/or the static trials 100 can be offered in a variety of dimensions without departing from the scope of the invention, and that the dimensions specifically identified and quantified herein are merely exemplary. Moreover, it should be understood that the set of static trials 100 need not include the same number of trials for each artificial intervertebral disc in the set of artificial intervertebral discs, but rather, none, one, or more than one trial can be included in the trial set for any particular artificial intervertebral disc in the set.

Each of the plurality of static trials preferably further includes features that can be used by the static trial holder (described below), the inserter/impactor (described below), and the repositioners/extractors (described below). With regard to a feature that can be used by the static trial holder, each static trial preferably includes a recess that can be gripped by the opposing semicircular extents of the static trial holder. Preferably, this recess forms an annular groove that establishes a cylindrical trunk between the baseplates of the static trial, such that the baseplates extend as flanges from either end of the cylindrical trunk. Accordingly, preferably, the opposing semicircular extents each have a thickness smaller than the width of the annular groove, and as such fit into the annular groove to grip the cylindrical trunk between them.

With regard to features that can be used by the inserter/impactor, each static trial (and each artificial intervertebral disc that the trials approximate) preferably includes an anteriorly facing flat surface, flanked by two anteriolaterally facing flat surfaces (one on each side of the anteriorly facing flat surface), and, to provide for holding of the static trial or disc for an anterior insertion approach, a hole spaced from the anteriorly facing flat surface, the hole having a longitudinal axis parallel to the anteriorly facing flat surface. The holding pin of the inserter/impactor fits within the hole, and the angled flat surfaces of the static trial or disc fit against the correspondingly angled flat surfaces of the inserter/impactor, and operation of the inserter/impactor pulls the holding pin toward the flat surface of the inserter/impactor opposite the pin, to rigidly hold the static trial or disc by the baseplate. When the static trial is held in this manner, rotation of the static trial or disc about a longitudinal axis (e.g., in the case of the trials, an axis parallel to the longitudinal axis of the cylindrical trunk) relative to the inserter/impactor is prevented by interference of the corners of the static trial's or disc's flat surfaces and the corners of the inserter/impactor's flat surfaces, similar to the manner in which a wrench holding a nut prevents rotation of the nut relative to the wrench. Further, the holding of the static trial or disc in this manner allows for some repositioning of the static trial or disc in the intervertebral space via rotation of the static trial or disc in either direction about the longitudinal axis of the intervertebral space.

Preferably, both of the baseplates of the static trial or disc have similarly configured flat surfaces, and both baseplates' flat surfaces fit against the angled flat surfaces of the inserter/impactor to provide for a more secure holding of the static trial or disc by the inserter/impactor. Also preferably, in order to provide for a holding of the static trial or disc for two additional (here, anteriolateral) insertion approaches, each static trial or disc also include two additional holes, one spaced apart from one of the anteriolaterally facing flat surfaces, and the other spaced apart from the other of the anteriolaterally facing flat surfaces. Accordingly, operation of the inserter/impactor can fit the holding pin into either of these two additional holes, and hold the anteriolaterally facing flat surface (the one associated with the hole into which the pin is fit) of the static trial or disc against the flat surface of the inserter/impactor opposite the pin. It should be understood that preferably, in order to facilitate these two additional approaches, the angle separating the anteriorly facing flat surface of the static trial or disc and one of the anteriolaterally facing flat surfaces of the static trial or disc is equal to the angle separating the anteriorly facing flat surface and the other of the anteriolaterally facing flat surfaces.

With regard to features that can be used by the repositioners/extractors, each static trial (and each artificial intervertebral disc that the trials approximate) preferably includes at least two holes extending longitudinally into one of the baseplates of the trial or disc from the inwardly facing surface of the baseplate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

As discussed in greater detail below with regard to the repositioners/extractors, in order to engage two of the holes, each repositioner/extractor has two pins extending in parallel from a central shaft, perpendicular to the longitudinal axis of the central shaft. The pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating of the central shaft of the repositioner/extractor about its distal end, about an axis parallel to the longitudinal axes of the pins.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles.

As described in greater detail below, three repositioner/extractors are illustrated and described (symmetric, offset left, and offset right) for example, and, for example, two hole configurations are illustrated and described. A first hole configuration includes the hole configuration described above, that is, three holes on one of the baseplates (e.g., the lower baseplate), the holes being configured so that a first hole is located in the anterior-posterior plane, and the adjacent (second and third) holes are located in respective opposing anteriolateral planes on either side of the first hole. A second hole configuration includes four holes on one of the baseplates (e.g., the upper baseplate), the holes being configured so that first and second holes straddle the anterior-posterior plane, a third hole is located so that the third hole and the first hole straddle one of the opposing anteriolateral planes, and a fourth hole is located so that the fourth hole and the second hole straddle the other of the opposing anteriolateral planes.

With further regard to the static trial holder described herein, the static trial holder is provided primarily for use in holding, inserting, removing, and otherwise manipulating the static trials described herein. Preferably, the static trial holder has a pair of opposing prongs that open away from one another and close toward one another. Each of the prongs has a semicircular extent and the semicircular extents face one another to define a circular holding enclosure that is useful for capturing the cylindrical trunk of the static trial between them. The prongs are spring biased toward a neutral position such that the holding enclosure is spring biased to a receptive state in which the cylindrical trunk can be snapped into (or out of) the holding enclosure by temporarily placing the holding enclosure in an expanded state (by forcing the cylindrical trunk against the mouth of the enclosure) that allows passage of the cylindrical trunk through the mouth of the enclosure. Once the cylindrical trunk is in the enclosure, the holding enclosure can be placed in a contracted state, or locked, where the trial is more securely held, so that the trial will not escape the holding enclosure as it is experiencing greater forces while being inserted and removed from the intervertebral space. This locking is effected by rotating a sleeve that surrounds the prongs. The bore of the sleeve is configured to press the prongs together when the sleeve is rotated a quarter turn, and to allow them to separate when the sleeve is again rotated a quarter turn (in either direction). The sleeve is biased toward stopping its rotation at either the "locked" or "unlocked" states of the holding enclosure, by the cooperation of recesses on the extension's outer surface and corresponding spring plungers radially disposed to project from the sleeve's inner surface. It should be understood that when the static trial is being held (either when the holding enclosure is in its receptive state or in its contracted state), because the semicylindrical extents fit within the annular groove of the static trial, the static trial will not escape from the enclosure along the longitudinal axis of the cylindrical trunk. While the static trial holder is discussed herein as primarily used for manipulating the static trials, it preferably is also useful for manipulating the distraction spacers described in the '127 application, in that the semicircular extents of the pincers preferably also interact with the annular grooves and cylindrical trunks of those distraction spacers in the same manner as described herein.

With regard to the dynamic trial described herein, the dynamic trial is provided primarily for distracting an intervertebral space according to the procedures described herein and/or for determining the appropriate size of an artificial intervertebral disc to be implanted (or whether a particular size can be implanted) into the distracted intervertebral space. While the distraction systems and methods described in the '127 application are also useful for distracting an intervertebral space, the dynamic trial is provided as an additional or alternate distraction tool. Further, while the static trials described herein as useful for determining the appropriate size of an artificial intervertebral disc to be implanted (or whether a particular size can be implanted), the dynamic trial is provided as an additional or alternate sizing tool.

The dynamic trial preferably includes a shaft having a bifurcated trial at a distal end. Each half of the bifurcated trial preferably has on its outwardly facing surface a convex dome that is shaped like the convex dome of the corresponding baseplate of the artificial intervertebral disc that the dynamic trial approximates. The shaft includes an inner shaft portion that centrally divides into upper and lower distal extensions that, from the point of division to their distal ends, are each biased toward positions in which they converge toward one another. The lower distal extension is connected to the lower half of the bifurcated trial, and the upper distal extension is connected to the upper half of the bifurcated trial. Preferably, the upper half is adjustably connected to the upper distal extension by a pivot pin that allows the upper half to rotate about a lateral axis that passes through the longitudinal and lateral center of the bifurcated trial. This axis of rotation allows the upper half, when separating from the lower half, to adjust to the orientation of the upper vertebral bone without causing the bone to hinge relative to the lower vertebral bone. In order to effect the separation of the upper and lower halves, the shaft further includes an outer shaft potion that is translatable adjacent the inner shaft portion, the outer shaft portion having a pin that passes between the distal extensions.

The outer shaft portion is preferably translatable distally by the forward movement of a control knob near the proximal end of the shaft, and translatable proximally by backward movement of the control knob. As the outer shaft portion is pushed distally, the pin is pushed distally to overcome the bias of the divided extensions to separate them and correspondingly separate the halves of the bifurcated trial. Preferably, markings are provided on the inner shaft portion to quantify the depth (to which the bifurcated trial has been expanded) corresponding to the distance that the outer shaft portion has been translated with respect to the inner shaft portion. It is anticipated that the pushing force required to separate the halves will increase as they separate, due to the compression of the spine seeking to close the intervertebral space and the annulus seeking to prevent the adjacent vertebral discs from separating beyond a certain point. Therefore, to provide a mechanical advantage to the operator in the event that greater distraction is required, but the operator cannot push the control knob farther with unaided human effort, an fine control knob is provided. The fine control knob is preferably threaded onto the proximal end of the inner shaft portion, proximal to the control knob. Thus, rotation of the fine control knob about the longitudinal axis of the inner shaft portion will cause the body of the fine control knob to press against the control knob to move it farther distally. The interference of the threads of the fine control knob-inner shaft portion interface prevents the fine control knob from backing up proximally unless the fine control knob is reverse rotated to effect that result. Finally, the proximal end of the shaft is preferably flanged to serve as a slap hammer for impaction, if necessary for proper positioning of the bifurcated trial, and/or forced extraction of the bifurcated trial.

With further regard to the inserter/impactor described herein, the inserter/impactor is provided primarily for holding, inserting, repositioning, removing, impacting, extracting, and otherwise manipulating an artificial intervertebral disc (or static trial) having features suitable for being manipulated by the inserter/impactor. Exemplary suitable artificial intervertebral discs are described in the '160 application with regard to FIGS. 8$a$-$y$, 9$a$-$t$, 10$a$-$t$, 11$a$-$j$, and 12$a$-$o$ thereof and by the accompanying descriptions therefor (e.g., embodiments identified as the first, second, third, fourth, and fifth preferred embodiments of the fourth embodiment family, etc.). Regarding the features suitable for being manipulated by the inserter/impactor, such features include those discussed above as being suitable features on the static trials and artificial intervertebral disc, namely, an anteriorly facing flat surface on the second (e.g., lower) baseplate of the trial or disc, flanked by two anterolaterally facing flat surfaces (one on each side of the anteriorly facing flat surface), and, to provide for holding of the trial or disc for an anterior insertion approach, a hole spaced from the anteriorly facing flat surface, the hole having a longitudinal axis parallel to the anteriorly facing flat surface.

The inserter/impactor includes a shaft having a distal end that has angled flat surfaces corresponding to and fittable against the angled flat surfaces of the static trial or artificial intervertebral disc, and a holding pin that extends from the center flat surface along a longitudinal axis of the shaft, the pin having a distal end that bends downward. The holding pin is spring loaded in a central channel of the shaft, so that it is biased toward and against the central flat surface (preferably, the bent end of the pin prevents it from entering the central channel). A flange, mechanically connected to the pin and translating adjacent the shaft, can be pushed distally to overcome the bias of the spring to space the pin away from the central flat surface. In this position, the pin can be inserted in the hole in the baseplate of the artificial intervertebral disc. Releasing the knob allows the spring to pull the pin back, causing the anteriorly facing surface of the baseplate to be held against the central flat surface of the inserter/impactor and the anterolaterally facing flat surfaces of the artificial intervertebral disc to be held against the other corresponding flat surfaces of the inserter/impactor. A knob on the inserter/impactor can be rotated about the longitudinal axis of the shaft to pull the pin tighter and lock its position to more securely hold the baseplate, and reverse rotated to unlock and loosen the pin.

When the static trial or artificial intervertebral disc is held in this manner, rotation of the trial or disc about its longitudinal axis relative to the inserter/impactor is prevented by interference of the corners of the trial's or disc's flat surfaces and the corners of the inserter/impactor's flat surfaces, similar to the manner in which a wrench holding a nut prevents rotation of the nut relative to the wrench. Further, the holding of the trial or disc in this manner allows for some repositioning of the trial or disc in the intervertebral space via rotation of the trial or disc in either direction about the longitudinal axis of the intervertebral space.

Preferably, both of the baseplates of the static trial or disc have similarly configured and oriented flat surfaces, and both baseplates' flat surfaces fit against the angled flat surfaces of the inserter/impactor, to provide for a more secure holding of the static trial or disc by the inserter/impactor.

Also preferably, in order to provide for a holding of the static trial or disc for two additional (here, anteriolateral) insertion approaches, each static trial or disc also includes two additional holes, one spaced apart from one of the anteriolaterally facing flat surfaces, and the other spaced apart from the other of the anteriolaterally facing flat surfaces. Accordingly, operation of the inserter/impactor can fit the holding pin into either of these two additional holes, and hold the associated anteriolaterally facing flat surface (the one associated with the hole into which the pin is fit) of the static trial or disc against the flat surface of the inserter/impactor opposite the pin. It should be understood that preferably, in order to facilitate these two additional approaches, the angle separating the anteriorly facing flat surface of the static trial or disc and one of the anteriolaterally facing flat surfaces of the static trial or disc is equal to the angle separating the anteriorly facing flat surface and the other of the anteriolaterally facing flat surfaces.

Also preferably, as shown the baseplates of each of the plurality of static trials are appropriately lordotically angled relative to one another to ease insertion of the static trial or artificial intervertebral disc into the intervertebral space and to mimic how the artificial intervertebral disc will typically be oriented as it is being inserted.

With further regard to the repositioners/extractors described herein, each repositioner/extractor is provided primarily for repositioning and/or extracting a static trial or artificial intervertebral disc having features suitable for being manipulated by the repositioner/extractor. Exemplary suitable artificial intervertebral discs are described in the '160 application with regard to FIGS. 8a-y, 9a-t, 10a-t, 11a-j, and 12a-o thereof and by the accompanying descriptions therefor (e.g., embodiments identified as the first, second, third, fourth, and fifth preferred embodiments of the fourth embodiment family, etc.). Regarding the features suitable for being manipulated by each repositioner/extractor, such features include at least two holes extending longitudinally into one of the baseplates of the static trial or artificial intervertebral disc from the inwardly facing surface of the baseplate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

In order to engage the two holes, each repositioner/extractor has two pins extending in parallel from a central shaft, perpendicular to the longitudinal axis of the central shaft. The pins are spaced to engage the two holes simultaneously, and each pin has a diameter smaller than the diameter of the hole it is to engage. Therefore, the pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating of the central shaft of the repositioner/extractor about its distal end, about an axis parallel to the longitudinal axes of the pins. A handle at a proximal end of the central shaft is useful for pushing or pulling on the shaft. A flange adjacent the proximal end of the shaft is useful for impaction (either with a distally directed force or a proximally directed force), if necessary to manipulate the shaft.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles.

With further regard to the leveler described herein, the leveler is provided primarily for establishing a parallel orientation of the baseplates (relative to one another), and/or securing the purchase of the stabilizing spikes, of an artificial intervertebral disc having features suitable for being manipulated by the leveler. Exemplary suitable artificial intervertebral discs are described in the '160 application with regard to FIGS. 8a-y, 9a-t, 10a-t, 11a-j, and 12a-o thereof and by the accompanying descriptions therefor (e.g., embodiments identified as the first, second, third, fourth, and fifth preferred embodiments of the fourth embodiment family, etc.). Regarding the features suitable for being manipulated by the leveler, such features include suitably formed inwardly facing surfaces of the baseplates of the artificial intervertebral disc.

More particularly, the leveler includes a shaft having a forked distal end formed by two opposing tongs that are symmetric to one another about a longitudinal axis of the shaft. Each of the tongs has an extent that initially curves laterally outward away from the shaft and from the other tong's extent, to define a central pocket forward of the shaft between the tongs' extents. Each tong's extent then resumes a distal direction to become parallel to the shaft and to the other tong's extent.

Each tong's extent has an upper surface and a lower surface. The upper surface is preferably shaped to conform against the inwardly facing surface of a first (e.g., upper) baseplate of an artificial intervertebral disc, and the lower surface is preferably shaped to conform against the inwardly facing surface of a second (e.g., lower) baseplate of the artificial intervertebral disc, so that insertion of the forked distal end of the leveler between the baseplates, with the central pocket of the distal end avoiding the central portion of the artificial intervertebral disc, and with the upper and lower surfaces so engaging the inwardly facing surfaces of the baseplates, causes the baseplates to be placed in parallel orientation with respect to one another. A handle is provided at a proximal end of the shaft for pushing, pulling, and otherwise manipulating the leveler as needed.

When the artificial intervertebral disc is inserted into the intervertebral space, its baseplates will typically be lordotically angled with respect to one another. The leveler can be applied to the artificial intervertebral disc to bring the baseplates parallel to one another. The forked distal end of the leveler is inserted so that the tongs' extents are placed between the inwardly facing surfaces of the baseplates, and so that the central pocket of the leveler avoids that portion of the artificial intervertebral disc that joins the baseplates. As the leveler is inserted, the tongs act as wedges to force the posterior portions of the baseplates away from one another. Accordingly, as the posterior portions are being separated, the stabilizing spikes on the outwardly facing surfaces of the baseplates find or secure their purchase in the hard bone of the outer ring of the vertebral body endplates. When the forked distal end is fully seated, the extents of the tongs hold the baseplates parallel to one another, and so that the spikes are fully engaged in the endplates.

BRIEF DESCRIPTION OF THE DRAWINGS

FIGS. 1g-n show front (FIG. 1g), side cutaway (FIG. 1h), top (FIG. 1i), side cutaway (FIG. 1j), bottom cutaway (FIG. 1k), top cutaway (FIG. 1l), bottom perspective (FIG. 1m), and top perspective (FIG. 1n) views of an exemplary artificial intervertebral disc of the present invention.

FIGS. 2a-k show top (FIG. 2a), side (FIG. 2b), perspective (FIG. 2c), disassembly (FIG. 2d-j), and side cutaway (FIG. 2k) views of a static trial holder of the present invention.

FIGS. 5v-dd show exemplary various possible repositioner/extractor approach angles with a four hole configuration of the present invention.

DETAILED DESCRIPTION OF THE PREFERRED EMBODIMENTS

Figure 1A:
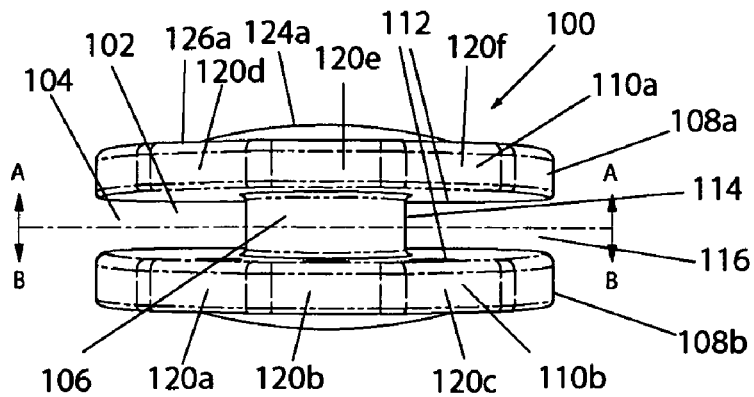
FIGS. 1a-f show front (FIG. 1a), side (FIG. 1b), perspective (FIG. 1c), top (FIG. 1d), bottom cutaway (FIG. 1e) and top cutaway (FIG. 1f) views of a static trial of the present invention.
Figure 1B:
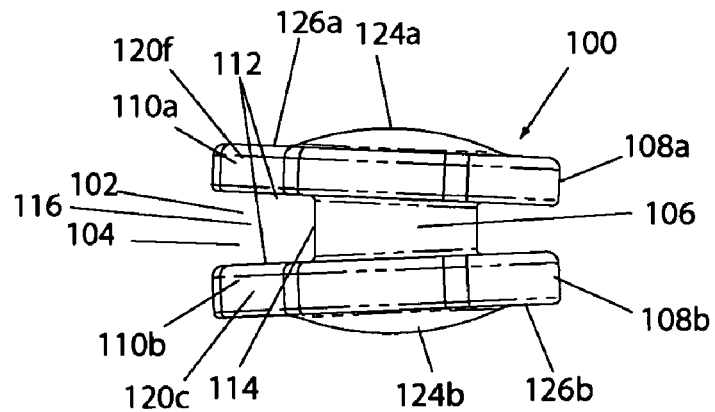
Figure 1C:
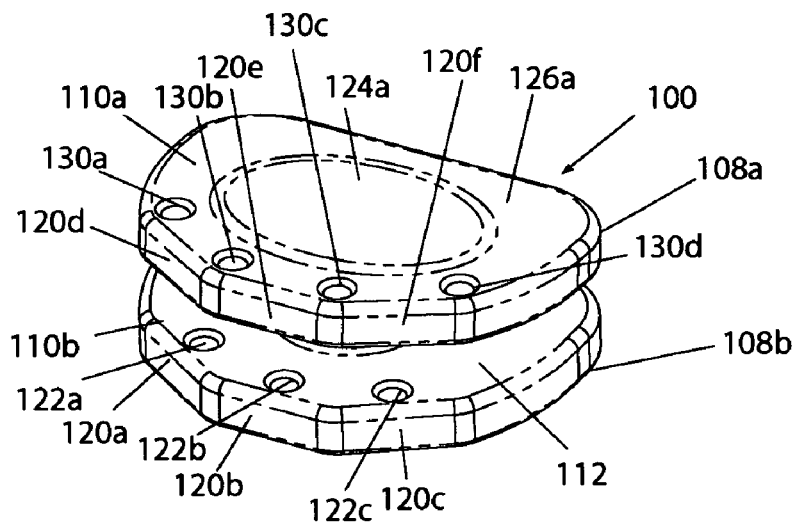
Figure 1D:
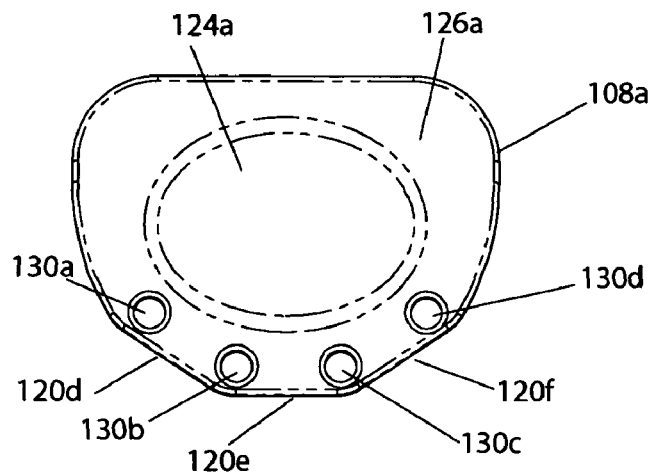
Figure 1E:
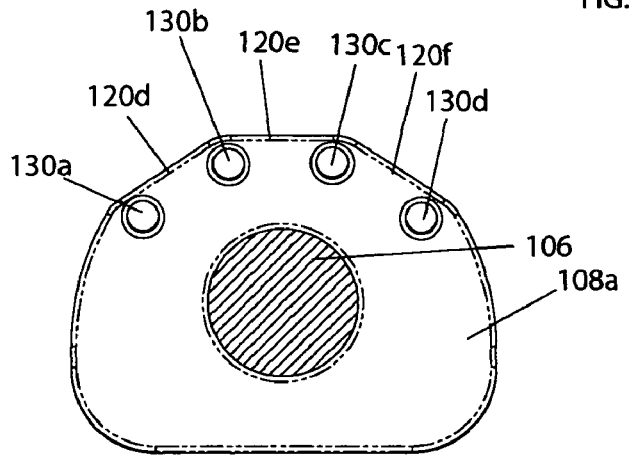
Figure 1F:
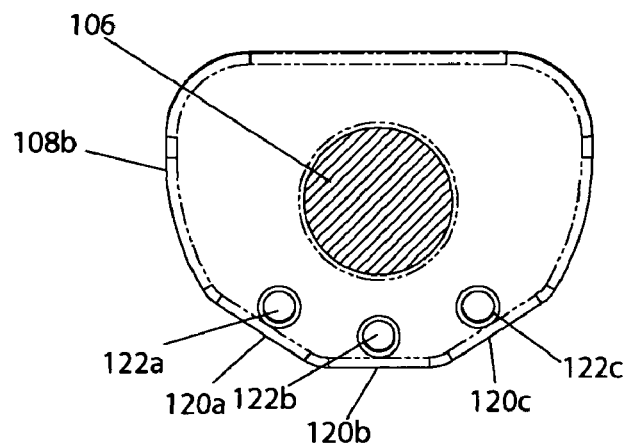
Figure 1K:
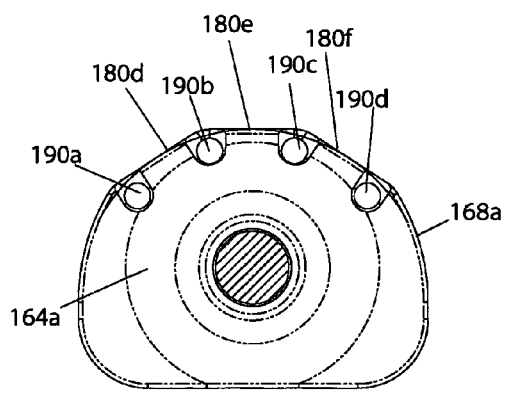
Figure 1L:
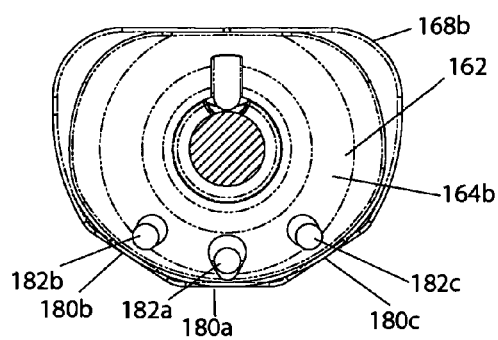
Figure 1M:
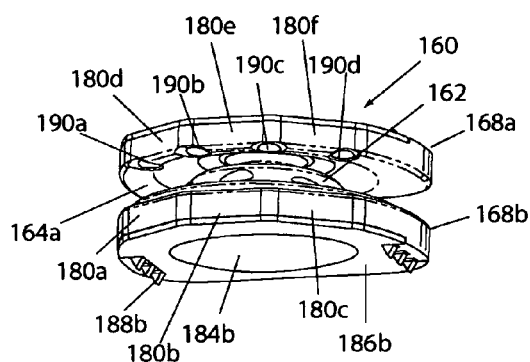
Figure 1N:
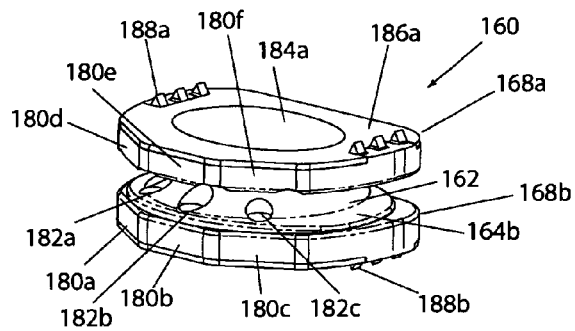
Figure 2A:
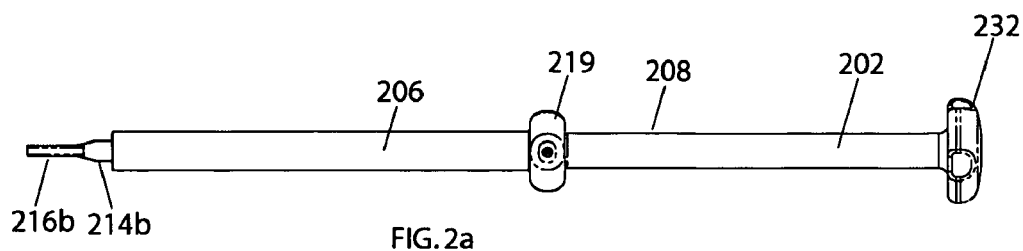
Figure 2B:
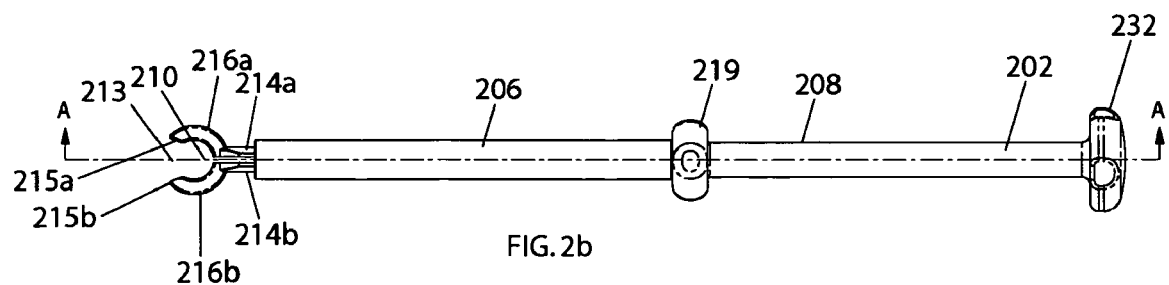
Figure 2C:
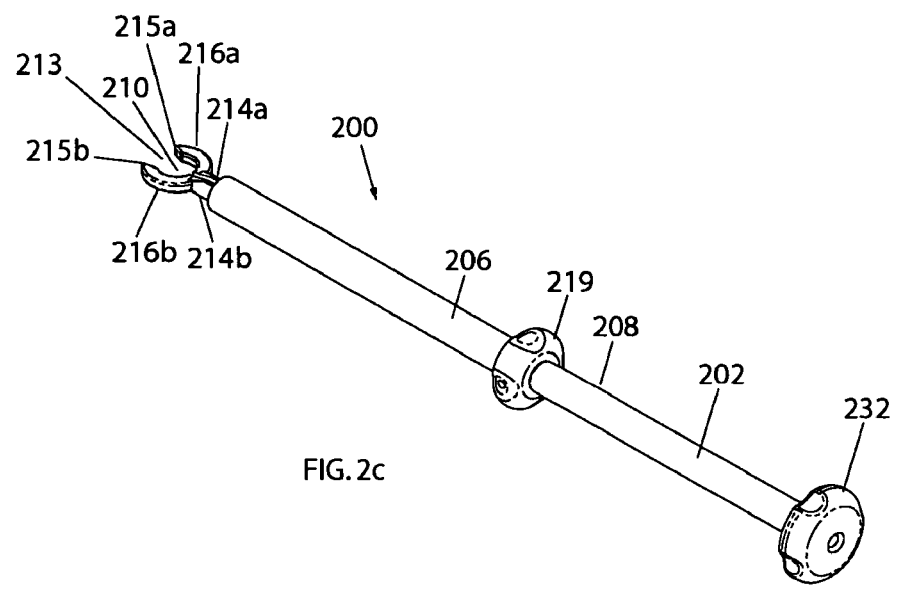
Figure 3A:
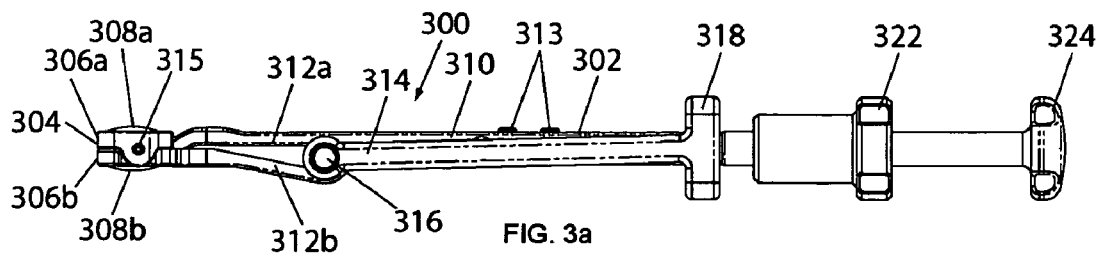
FIGS. 3a-d show side (FIG. 3a), top (FIG. 3b), side cutaway (FIG. 3c), and perspective (FIG. 3d) views of a dynamic trial of the present invention.
Figure 3B:
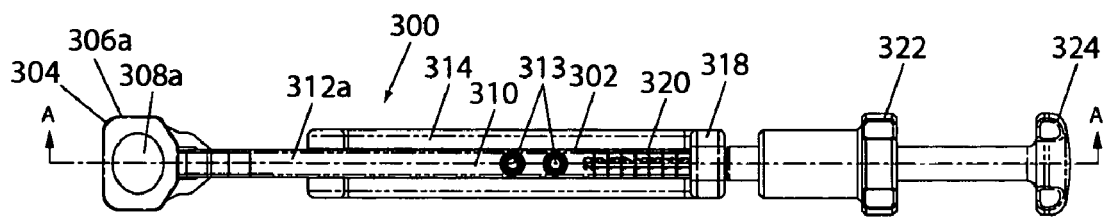
Figure 3C:
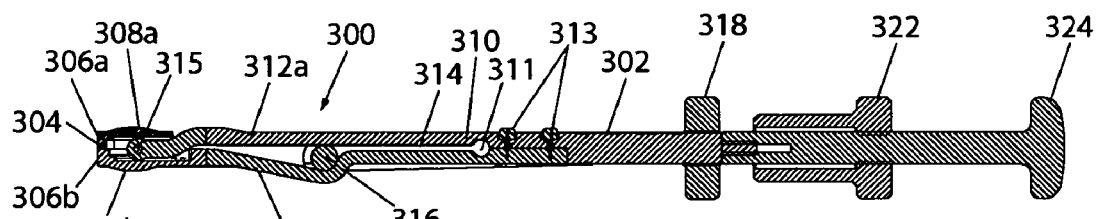
Figure 3D:
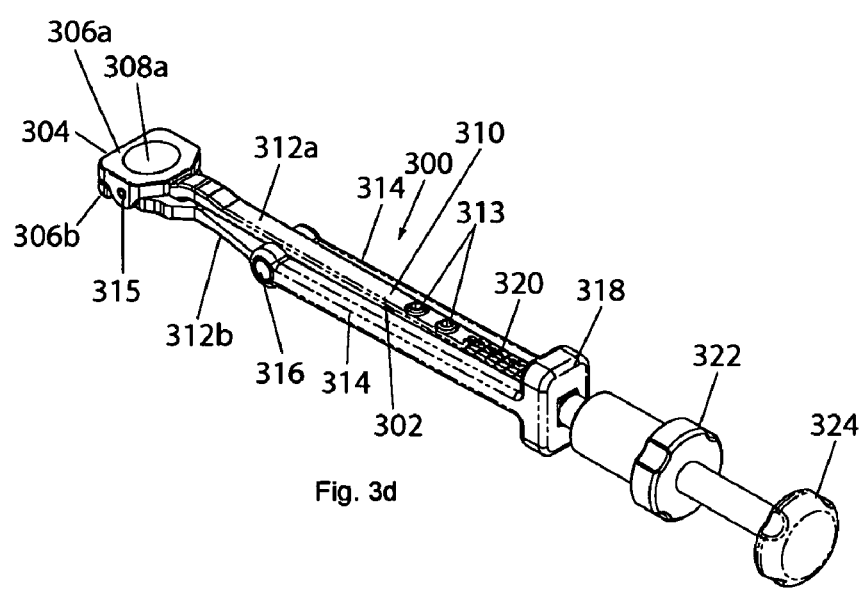

While the invention will be described more fully hereinafter with reference to the accompanying drawings, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

A preferred embodiment of a static trial of the present invention, and a preferred embodiment of an artificial intervertebral disc of the present invention, both for use with the instrumentation of the present invention, will now be described.

Referring now to FIGS. 1a-f, a static trial of the present invention is shown in front (FIG. 1a), side (FIG. 1b), perspective (FIG. 1c), top (FIG. 1d), bottom cutaway (FIG. 1e), and top cutaway (FIG. 1f) views. Referring now to FIGS. 1g-n, an artificial intervertebral disc of the present invention is shown in front (FIG. 1g), side cutaway (FIG. 1h), top (FIG. 1i), side cutaway (FIG. 1j), bottom cutaway (FIG. 1k), top cutaway (FIG. 1l), bottom perspective (FIG. 1m), and top perspective (FIG. 1n) views.

It should be understood that the illustration and reference herein to the artificial intervertebral disc shown in FIGS. 1g-n is merely to show an example of one type of artificial intervertebral disc that is contemplated by, encompassed by, and suitable for use with, the present invention, and that such illustration and reference herein is not meant to limit the scope of the present invention or limit the uses of the present invention. Rather, any other artificial intervertebral disc (or any other orthopedic device) having suitable features for being manipulated by the instrumentation and methods described herein are contemplated by the present invention. Indeed, the features suitable for manipulation (e.g., angled flat surfaces with adjacent holes) are encompassed by the present invention, regardless of to what orthopedic device they may be applied. Other exemplary suitable artificial intervertebral discs include, but are not limited to, the artificial intervertebral discs described in the '160 application with regard to FIGS. 8a-y, 9a-t, 10a-t, 11a-j, and 12a-o thereof and by the accompanying descriptions therefor (e.g., embodiments identified as the first, second, third, fourth, and fifth preferred embodiments of the fourth embodiment family, etc.). It should be noted that, as can be seen from FIGS. 1g-n, that the artificial intervertebral disc shown in FIGS. 1g-n has features similar to those of these other suitable artificial intervertebral discs of the '160 application, and it should be understood that such similar features are structurally and functionally as described in the '160 application. Such similar features include an inwardly facing surface 164a of the upper baseplate 164a, and a convex structure 162 on the lower baseplate 168b, the convex structure 162 having an inwardly facing surface 164b.

And, while the instrumentation described herein (e.g., the static trials, static trial holder, dynamic trial, inserter/impactor, repositioners/extractors, and leveler) will be discussed for use with the artificial intervertebral disc of FIGS. 1g-n, such discussions are merely by way of example and not intended to be limiting of their uses. Thus, it should be understood that the tools can be used with any of the artificial intervertebral discs disclosed in the '160 application, or any other artificial intervertebral disc having (or being modifiable or modified to have) suitable features therefor. Moreover, it is anticipated that the features of the artificial intervertebral disc (e.g., the flat surfaces and accompanying holes) and/or the static trials (e.g., the cylindrical trunks and flat surfaces and accompanying holes) that are used by the tools discussed herein to hold and/or manipulate these devices (such features, it should be noted, were first shown and disclosed in the '160 application and the '127 application) can be applied, individually or collectively or in various combinations, to other trials, spacers, artificial intervertebral discs or other orthopedic devices as stand-alone innovative features for enabling such trials, spacers, artificial intervertebral discs, or other orthopedic devices to be more efficiently and more effectively held and/or manipulated by the tools described herein or by other tools having suitable features. In addition, it should be understood that the invention encompasses artificial intervertebral discs, spacers, trials (static or dynamic), and/or other orthopedic devices, that have one or more of the features disclosed herein, in any combination, and that the invention is therefore not limited to artificial intervertebral discs, spacers, trials, and/or other orthopedic devices having all of the features simultaneously.

A plurality of static trials 100 are provided primarily for use in determining the appropriate size of an artificial intervertebral disc to be implanted (or whether a particular size of the artificial intervertebral disc can be implanted) into the distracted intervertebral space (e.g., the artificial intervertebral disc 160 of FIGS. 1*g-n*). Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. Accordingly, preferably, each of the plurality of static trials 100 for use with a particular plurality of differently sized artificial intervertebral discs would have a respective width and depth dimension set corresponding to the width and depth of a respective one of the plurality of differently sized artificial intervertebral discs. For example, the plurality of static trials 100 for use with the set of artificial intervertebral discs described for example could include static trials 100 having widths being either 35 mm or 40 mm, and depths ranging from 14 mm to 18 mm in 1 mm increments, for a total of 10 static trials. It should be understood that the artificial intervertebral discs and/or the static trials 100 can be offered in a variety of dimensions without departing from the scope of the invention, and that the dimensions specifically identified and quantified herein are merely exemplary. Moreover, it should be understood that the set of static trials 100 need not include the same number of trials for each artificial intervertebral disc in the set of artificial intervertebral discs, but rather, none, one, or more than one trial can be included in the trial set for any particular artificial intervertebral disc in the set.

Each of the static trials (the static trial 100 shown is exemplary for all of the static trials in the plurality of static trials; preferably the static trials in the plurality differ from one another only with regard to overall dimensions as described above) includes at least one feature that can be gripped by a tool. Suitable tools include, but are not limited to, the static trial holder 200 described below, the inserter/impactor 400 described below, and the repositioners/extractors 510, 520, 530, 540 described below. Specifically, the static trial 100 includes a recess 102 that can be gripped by the opposing semicircular extents 216*a-b* of the static trial holder 200. Preferably, this recess 102 forms an annular groove 104 that establishes a cylindrical trunk 106 between the upper and lower baseplates 108*a-b* of the static trial 100, such that the baseplates 108*a-b* extend as flanges 110*a-b* from either end of the cylindrical trunk 106. Accordingly, preferably, the opposing semicircular extents 216*a-b* each have a thickness smaller than the width of the annular groove 104, and as such fit into the annular groove 104 to grip the cylindrical trunk 106 between them.

In some embodiments, while not shown in FIGS. 1*a-f*, it is also preferable that the annular groove 104 radially widen outwardly, such that the walls 112 of the annular groove 104 are tapered toward one another with the increasing depth of the groove 104, such that the floor 114 of the groove 104 is more narrow than the opening 116 of the groove 104. Accordingly, preferably, in such embodiments, each semicircular extent 216*a-b* correspondingly radially widens outwardly, such that the thinner portion of the extent 216*a-b* fits closer to the floor 114 of the annular groove 104, so that the tapered surfaces of the extents 216*a-b* compress against the tapered walls 112 of the annular groove 104 when the static trial 100 is gripped by the static trial holder 200. This taper locking provides for a secure grip so that the static trial 100 can be manipulated accurately and efficiently.

In some embodiments, while not shown in FIGS. 1*a-f*, it is also preferable that the floor of the annular groove 104 of the cylindrical trunk 106 be ridged (e.g., have ridges that run parallel to the longitudinal axis of the cylindrical trunk), and the surfaces of the semicircular extents 216*a-b* of the static trial holder 200 that compress against the floor of the annular groove 104 when the static trial holder 200 grips the static trial 100 be correspondingly provided with ridges. The interlocking of the ridges of the static trial 100 with the ridges of the static trial holder 200 when the static trial 100 is gripped prevents rotation of the static trial 100 about the longitudinal axis of the cylindrical trunk 106 with respect to the static trial holder 200.

Additionally with regard to features that can be gripped by a tool, each of the static trials includes at least one feature that can be gripped by a tool that preferably is also used to grip the artificial intervertebral disc that the trial approximates. Suitable tools that can grip both the trial and the artificial intervertebral disc include, but are not limited to, the inserter/impactor 400 described below. Specifically, for being gripped by the inserter/impactor 400, each static trial 100 and artificial intervertebral disc 160 includes an anteriorly facing flat surface 120*b*, 180*b*, flanked by two anteriolaterally facing flat surfaces 120*a*,180*a* and 120*c*,180*c* (one on each side of the anteriorly facing flat surface 120*b*,180*b*), and, to provide for holding of the static trial 100 or disc 160 for an anterior insertion approach, a hole 122*b*,182*b* spaced from the anteriorly facing flat surface, the hole 122*b*,182*b* having a longitudinal axis parallel to the anteriorly facing flat surface 120*b*, 180*b*.

The holding pin 408 of the inserter/impactor 400 fits within the hole 122*b*,182*b*, and the angled flat surfaces 120*a-c*, 180*a-c* of the static trial 100 or disc 160 fit against the correspondingly angled flat surfaces 420*a-c* of the inserter/impactor 400, and operation of the inserter/impactor 400 pulls the holding pin 408 toward the flat surface 120*b*,180*b* of the inserter/impactor 400 opposite the pin 408, to rigidly hold the static trial 100 or disc 160 by the structure of the static trial 100 or disc 160 having the hole 122*b*,182*b* (e.g., the baseplate 108*b*,168*b*). When the static trial 100 or disc 160 is held in this manner, rotation of the static trial 100 or disc 160 about a longitudinal axis (of the static trial 100 or disc 160) relative to the inserter/impactor 400 is prevented by interference of the corners of the static trial's 100 or disc's 160 flat surfaces 120*a-c*,180*a-c* and the corners of the inserter/impactor's 400 flat surfaces 420*a-c*, similar to the manner in which a wrench holding a nut prevents rotation of the nut relative to the wrench. Further, the holding of the static trial 100 or disc 160 in this manner allows for some repositioning of the static trial 100 or disc 160 in the intervertebral space via rotation of the static trial 100 or disc 160 in either direction about the longitudinal axis of the intervertebral space.

Preferably, both of the baseplates of the static trial 100 or disc 160 have similarly configured flat surfaces. For example, the lower baseplate's 108*b*,168*b* flat surfaces 120*a-c*,180*a-c* have similarly configured and similarly oriented counterpart flat surfaces 120*d-f*, 180*d-f* on the upper baseplate 108*a*, 168*a*. Further preferably, both baseplates' 108*a-b*,168*a-b* flat surfaces 120*a-f*,180*a-f* face the angled flat surfaces 420*a-c* of the inserter/impactor 400 when the static trial 100 or disc 160 is held by the inserter/impactor 400. For example, as discussed below with regard to the inserter/impactor 400, in an anterior approach for the trial 100 (as shown in FIGS. 4*e-h*), 120*a* and 120*d* facing 420*a*,120*b* and 120*e* facing 420*b*, and 120*c* and 120*f* facing 420*c*, and in an anterior approach for the disc 160 (as shown in FIGS. 4*k-n*), 180*a* and 180*d* facing 420*a*, 180*b* and 180*e* facing 420*b*, and 180*c* and 180*f* facing 420*c*.

It should be noted that preferably, when the static trial 100 is held by the inserter/impactor 400, the flat surfaces 120*a-c* and the counterpart flat surfaces 120*d-f* are tightly held against the angled flat surfaces 420*a-c* of the inserter/impactor 400 as described above. It is also preferable that the baseplates 108*a-b* of each of the plurality of static trials 100 be appropriately lordotically angled relative to one another to ease insertion of the static trial 100 into the intervertebral space and to mimic how the artificial intervertebral disc 160 will typically be oriented as it is being inserted using the inserter/impactor 400, and to ease insertion of the static trial 100 into the intervertebral space. While not shown in FIGS. 1*a-f*, in some embodiments, when the static trials 100 are formed in such a lordotically oriented configuration, it is preferable that the flat surfaces 120*d-f* on the first (e.g., upper) baseplate 108*a* be parallel to the flat surfaces 120*a-c* of the second (e.g., lower) baseplate 108*b* in the static trial's 100 appropriately lordotically oriented configuration, so that when the static trial 100 is held tightly by the inserter/impactor 400, the flat surfaces 120*a-f* are flush with the flat surfaces 420*a-c* of the inserter/impactor 400 even though the baseplates 108*a-b* are lordotically angled with respect to one another.

By contrast, preferably, when the artificial intervertebral disc 160 is held by the inserter/impactor 400, the flat surfaces 180*a-c* are tightly held against the angled flat surfaces 420*a-c* of the inserter/impactor 400 as described above, but the counterpart flat surfaces 180*d-f* are loosely held against the angled flat surfaces 420*a-c* of the inserter/impactor 400. As such, the structure of the artificial intervertebral disc 160 having the counterpart flat surfaces 180*d-f* (e.g., the upper baseplate 168*a*) is able to angulate and rotate to a limited extent relative to the structure of the artificial intervertebral disc 160 having the flat surfaces 180*a-c*. This permits the artificial intervertebral disc 160 to adjust to the intervertebral space (e.g., to the angulation of the adjacent vertebral endplates, defining the intervertebral space, relative to one another) as it is being inserted thereinto. That is, typically, the adjacent vertebral endplates will be lordotically angled with respect to one another as a result of the intervertebral space being prepared and distracted. As the artificial intervertebral disc 160 is then inserted into the intervertebral space using the inserter/impactor 400, then, the baseplates 168*a-b* will be permitted to lordotically angle with respect to one another to squeeze into the intervertebral space.

Figure 4A:
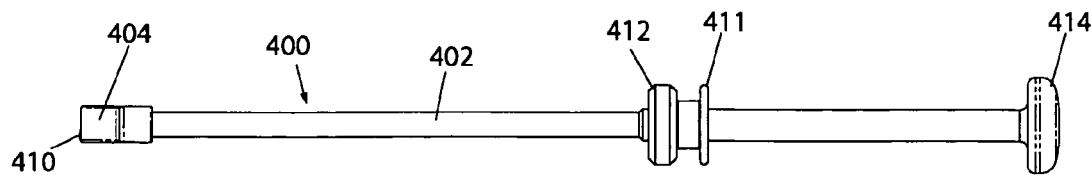
FIGS. 4a-d show side (FIG. 4a), top (FIG. 4b), side cutaway (FIG. 4c), and perspective (FIG. 4d) views of an inserter/impactor of the present invention.
Figure 4B:
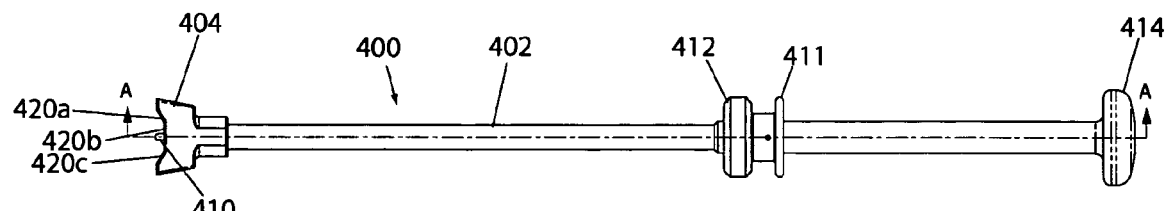
Figure 4C:
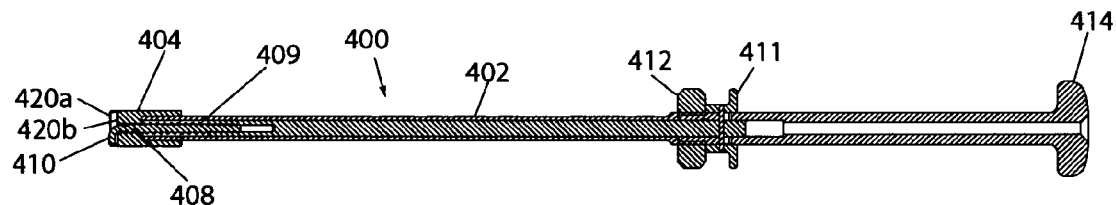
Figure 4D:
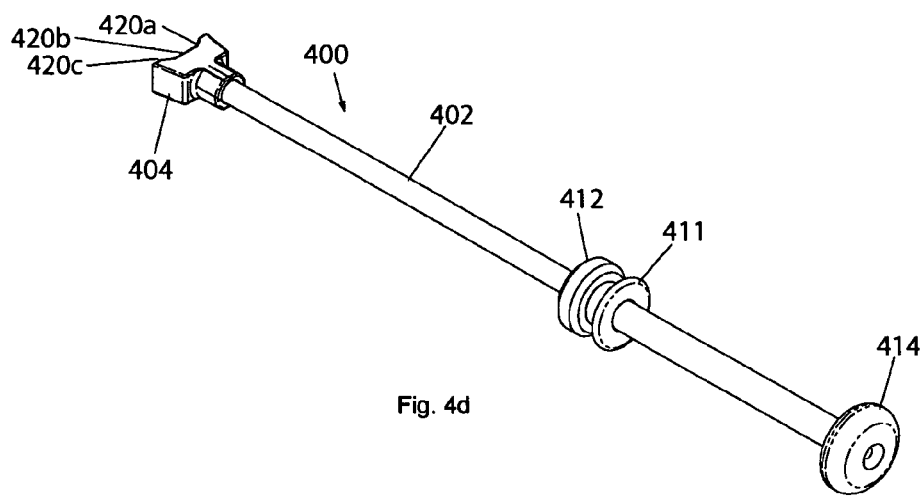
Figure 4E:
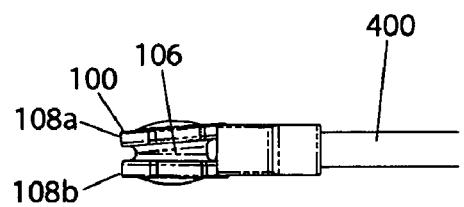
FIGS. 4e-h show side (FIG. 4e), top (FIG. 4f), side cutaway (FIG. 4g), and perspective (FIG. 4h) views of an inserter/impactor of the present invention holding a static trial of the present invention.
Figure 4F:
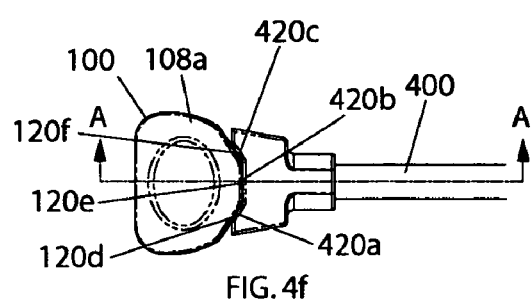
Figure 4H:
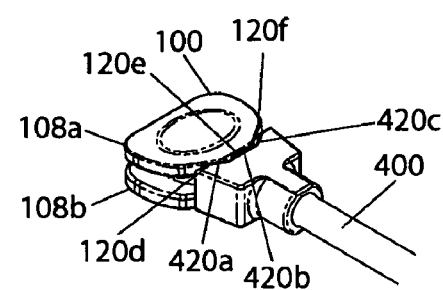
Figure 4G:
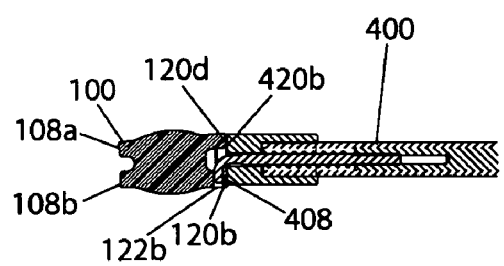
Figure 4I:
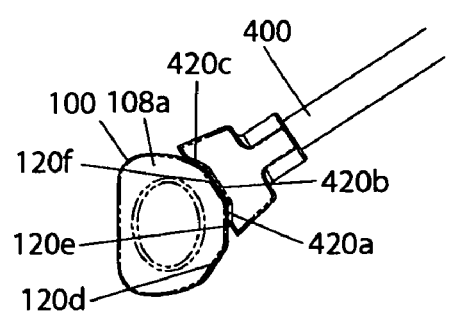
FIGS. 4i-j. show top views of an inserter/impactor of the present invention holding a static trial of the present invention in two alternative ways.
Figure 4J:
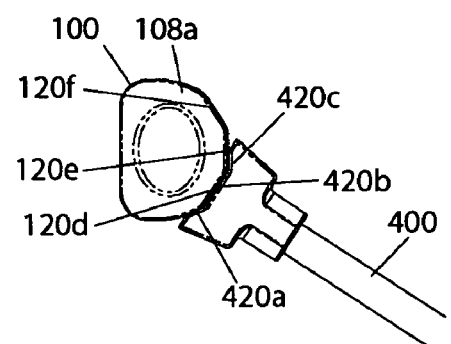
Figure 4K:
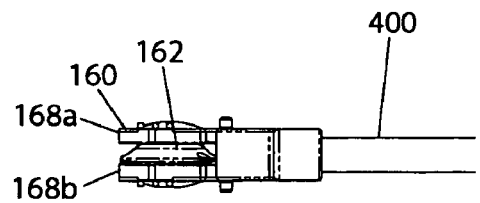
FIGS. 4k-n show side (FIG. 4k), top (FIG. 4l), side cutaway (FIG. 4m), and perspective (FIG. 4n) views of an inserter/impactor of the present invention holding an exemplary artificial intervertebral disc of the present invention.
Figure 4L:
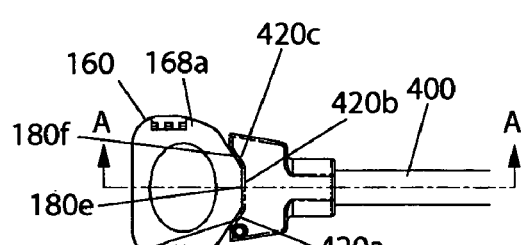
Figure 4N:
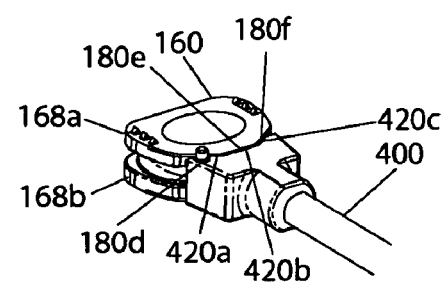
Figure 4M:
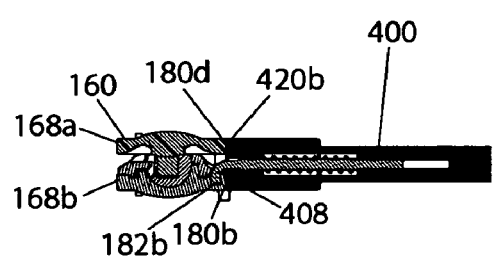
Figure 4O:
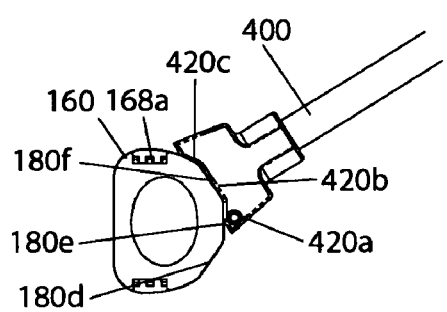
FIGS. 4o-p show top views of an inserter/impactor of the present invention holding an exemplary artificial intervertebral disc of the present invention in two alternative ways.
Figure 4P:
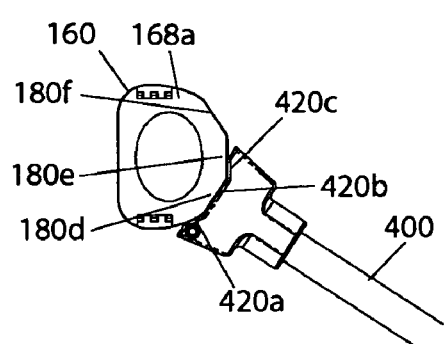

Also preferably, in order to provide for a holding of the static trial 100 or disc 160 for two additional (here, anterolateral) insertion approaches, each static trial 100 or disc 160 also includes two additional holes 122*a*,182*a* and 122*c*,182*c*, one (e.g., 122*a*,182*a*) spaced apart from one of the anterolaterally facing flat surfaces (e.g., 120*a*,180*a*), and the other (e.g., 122*c*,182*c*) spaced apart from the other of the anteriolaterally facing flat surfaces (e.g., 120*c*,180*c*). Accordingly, operation of the inserter/impactor 400 can fit the holding pin 408 into either of these two additional holes 122*a*,182*a* or 122*c*,182*c*, and hold the associated anterolaterally facing flat surface (the one associated with the hole into which the pin 408 is fit) of the static trial 100 or disc 160 against the flat surface of the inserter/impactor 400 opposite the pin 408. For example, as discussed below with regard to the inserter/impactor 400, in a first anterolateral approach for the trial 100 (as shown in FIG. 4*i*), 120*a* and 120*d* facing 420*b*, 120*b* and 120*e* not confronted, and 120*c* and 120*f* facing 420*a*, and a first anterolateral approach for the disc 160 (as shown in FIG. 4*o*), 180*a* and 180*d* facing 420*b*, 180*b* and 180*e* not confronted, 180*c* and 180*f* facing 420*a*. And, for example, as discussed below with regard to the inserter/impactor 400, in a second anterolateral approach for the trial 100 (as shown in FIG. 4*j*), 120*a* and 120*d* facing 420*c*, 120*b* and 120*e* facing 420*a*, and 120*c* and 120*f* not confronted, and a second anteriolateral approach for the disc 160 (as shown in FIG. 4*p*), 180*a* and 180*d* facing 420*c*, 180*b* and 180*e* facing 420*a*, 180*c* and 180*f* not confronted.

It should be understood that preferably, in order to facilitate these additional approaches, the angle separating the anteriorly facing flat surface of the static trial 100 or disc 160 and one of the anterolaterally facing flat surfaces of the static trial 100 or disc 160 is equal to the angle separating the anteriorly facing flat surface and the other of the anteriolaterally facing flat surfaces. Preferably, the surfaces are angled with respect to one another at an angle of 33.4 degrees.

It should also be understood that the inclusion of additional adjacent angulated surfaces (or placing the angulated surfaces in other locations on the trial or disc), and/or including corresponding holes adjacent to such surfaces, can provide the surgeon with additional approaches, e.g., other anterolateral approaches, directly lateral approaches, posterolateral approaches, and/or directly posterior approaches. For example, a trial or disc can have angled surfaces (and corresponding holes) along the entire perimeter of one or both of the baseplates, and thus enable the surgeon to engage the trial or disc from a number of angles, including anterior, posterior, lateral, anteriolateral, and posteriolateral angles.

Additionally with regard to features that can be gripped by a tool, each of the static trials includes at least one feature that can be gripped by a tool that preferably is also used to grip the artificial intervertebral disc that the trial approximates. Suitable tools that can grip both the trial and the artificial intervertebral disc include, but are not limited to, the repositioners/extractors 500, 510, 520, 530, 540 described below. Specifically, for being gripped by the repositioners/extractors, each static trial 100 and artificial intervertebral disc 160 includes at least two holes extending longitudinally into one of the baseplates of the static trial 100 or artificial intervertebral disc 160 from the inwardly facing surface of the baseplate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

As discussed in greater detail below with regard to the repositioners/extractors 500, 510, 520, 530, 540, in order to engage two of the holes, each repositioner/extractor has two pins extending in parallel from a central shaft, perpendicular to the longitudinal axis of the central shaft. The pins are spaced to engage the two holes simultaneously, and each pin has a diameter smaller than the diameter of the hole it is to engage. Therefore, the pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating of the central shaft of the repositioner/extractor about its distal end, about an axis parallel to the longitudinal axes of the pins. A handle at a proximal end of the central shaft is useful for pushing or pulling on the shaft. A flange adjacent the proximal end of the shaft is useful for impaction (either with a distally directed force or a proximally directed force), if necessary to manipulate the shaft.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles.

As described in greater detail below, three repositioner/extractors are illustrated and described (symmetric, offset left, and offset right) for example, and, for example, two hole configurations are illustrated and described. Referring again to FIGS. 1*a-n*, a first hole configuration includes the hole configuration described above, that is, three holes on one of the baseplates (e.g., the lower baseplate 108*b*,168*b*), the holes being configured so that a first hole 122*b*,182*b* is located in the anterior-posterior plane, and the adjacent (second 122*a*, 182*a* and third 122*c*,182*c*) holes are located in respective opposing anteriolateral planes on either side of the first hole 122*b*,182*b*. (This hole configuration is also shown in FIGS. 5*p-u*, each of which shows a top cutaway view of the artificial intervertebral disc 160 of FIGS. 1*g-n*, showing its lower baseplate 168*b*, having the first hole configuration, engaged by one of the repositioners/extractors 500,510,520. Each view of the lower baseplate 168*b* shows the first hole 182*b*, the second hole 182*a*, and the third hole 182*c* of the first hole configuration.)

Referring again to FIGS. 1*a-n*, a second hole configuration includes four holes on one of the baseplates (e.g., the upper baseplate 108*a*,168*a*), the holes being configured so that first (e.g., 130*c*,190*c*) and second (e.g., 130*b*,190*b*) holes straddle the anterior-posterior plane, a third hole (e.g., 130*d*,190*d*) is located so that the third hole and the first hole straddle one of the opposing anteriolateral planes, and a fourth hole (e.g., 130*a*,190*a*) is located so that the fourth hole and the second hole straddle the other of the opposing anteriolateral planes. (This hole configuration is also shown in FIGS. 5*v-dd*, each of which shows a bottom cutaway view of the artificial intervertebral disc of FIGS. 1*g-n*, showing its upper baseplate 168*a*, having the second hole configuration, engaged by one of the repositioners/extractors 500,510,520. Each view of the upper baseplate shows the first hole 190*c*, the second hole 190*b*, the third hole 190*d*, and the fourth hole 190*a*, of the second hole configuration.)

It should be understood that configurations having more or fewer holes, and in a variety of locations, are contemplated by the invention, and the detailed descriptions of only two hole configurations is not meant to limit the invention to only these two configurations. Importantly, the invention encompasses using a hole or any number of holes, bored at any suitable angle, whether parallel to other holes or not, in any number of locations on a spacer, a trial or an artificial intervertebral disc (not limited to locations on the baseplates), for purposes of enabling the spacer, trial, or disc to be gripped by a manipulation instrument (not limited to a repositioner/extractor) that engages the hole, and/or to enable the surgeon to work from a variety of approaches. For example, as described in more detail below, the first and second hole configurations described herein, in cooperation with the repositioner/extractors, provide the surgeon with the ability to work from a directly anterior approach, as well as several anteriolateral approaches. It should be understood that additional hole configurations can enable the surgeon to work from a directly posterior approach, posteriolateral approaches, directly lateral approaches, or anteriolateral approaches that are different that those illustrated. For example, the placement of one or more suitably spaced holes (or the addition of one or more holes) on the posterior edge, and/or one or both of the lateral edges of one or both of the baseplates, would enable the surgeon to use the repositioner/extractors of the present invention to achieve such approaches.

Thus, it can be seen that each of the repositioner/extractors can be used in more than one manner depending on the tool desired and the approach desired. These manners are described in greater detail below and illustrated in FIGS. 5*p-dd* with regard to the detailed description of the repositioners/extractors.

Also preferably, the baseplates 108*a-b* of each of the plurality of static trials 100 preferably has a convex dome 124*a-b* on its outwardly facing surface 126*a-b* that is shaped like the convex dome 184*a-b* on the outwardly facing surface 186*a-b* of the corresponding baseplate 168*a-b* of the artificial intervertebral disc 160 that the static trial 100 approximates. Preferably, each convex dome 124*a-b* is smooth, rather than having a porous coating that is preferred for the convex domes 184*a-b* of the artificial intervertebral disc 160, and each outwardly facing surface 126*a-b* does not have stabilizing spikes such as the stabilizing spikes 188*a-b* on the outwardly facing surfaces 186*a-b* of the artificial intervertebral disc 160. The omission of these device stabilizing and bone ingrowth encouraging structures and surfaces on the static trials 100 enables the surgeon to test the size of the artificial intervertebral disc 160 to be implanted without traumatically engaging the vertebral body endplates.

Accordingly, the surgeon can prepare and distract the intervertebral space, and then insert and remove at least one of the static trials (or more, as necessary) to find the size that is most appropriate for the intervertebral space.

A preferred embodiment of a static trial holder of the present invention will now be described.

Referring to FIGS. 2*a-c* and 2*k*, a static trial holder of the present invention is shown in side (FIG. 2*a*), top (FIG. 2*b*), perspective (FIG. 2*c*), and side cutaway (FIG. 2*k*) views. In addition, referring to FIGS. 2*d-f*, a sleeve of the static trial holder is shown in side cutaway (FIG. 2d), front (FIG. 2e), and back (with partial cutaway) (FIG. 2 views. In addition, referring to FIGS. 2g-i, an extension of the static trial holder is shown in top (FIG. 2g), proximal cutaway (FIG. 2h), side (FIG. 2i), and distal cutaway (FIG. 2j) views.

The static trial holder 200 is provided primarily for use in holding, inserting and removing the static trials described herein, or distraction spacers having suitable features therefor, such as the distraction spacers disclosed in the '127 application.

More specifically, the static trial holder 200 includes a handle 202, an extension 204, and a sleeve 206. As shown in FIG. 2k, the handle 202 and the extension 204 are fixed to one another (preferably by the distal end of the handle 202 being fixed to the proximal end of the extension 204) to form a shaft 208. The sleeve 206 surrounds the extension 204 and is rotatable with respect to the handle 202 and the extension 204 about the longitudinal axis of the shaft 208. The handle 202 preferably has an flange 232 at its proximal end for use in applying a distally or proximally directed force to get the static trial 100 (or distraction spacer) into or out of the intervertebral space, and/or for use in helping the surgeon rotate the sleeve 206 with respect to the extension 204 (by gripping the flange 232 and the control knob 219 described below).

The distal end of the extension 204 forms a contractable and expandable holding enclosure 210 in that the distal end is divided at a fulcrum 212 into two prongs 214a-b, each of which terminates in a semicircular extent 216a-b, each of which has a tapered end 215a-b. The extents 216a-b are oriented such that the tapered ends 215a-b face one another to define a radially inwardly tapering mouth 213, and such that the semicircular openings oppose one another to define the holding enclosure 210. The prongs 214a-b are spring biased toward a neutral position (preferably by the formation of the fulcrum 212 in combination with the strength of the material of which the extension 204 is made) such that the holding enclosure 210 is spring biased to a receptive state (described below), but the prongs 214a-b can be brought together to contract the holding enclosure 210 to a contracted state, (described below) or the prongs 214a-b can be further separated to expand the holding enclosure 210 to an expanded state (described below).

When the holding enclosure 210 is in the receptive state, the width of the mouth 213 of the holding enclosure 210 does not accommodate the diameter of the cylindrical trunk 106 of the static trial 100 (or distraction spacer) for passage therethrough. However, from this receptive state, the mouth 213 can be temporarily widened (placing the holding enclosure 210 in its expanded state) to accommodate the diameter (for passage of the cylindrical trunk 106 through the mouth 213), if a sufficient force is applied to overcome the neutral position bias of the prongs 214a-b and thus widen the mouth 213. (Preferably, there is enough space between the outer surfaces of the prongs 214a-b and the inner surface of the bore 218 of the sleeve, when the prongs 214a-b are in their neutral position, so that the prongs 214a-b can be separated without interference.) The sufficient force can be applied by pressing the cylindrical trunk 106 against the tapered ends 215a-b of the mouth 213, in that the separating force component of the radially inward force of the pressing will be applied to the semicircular extents 216a-b by the taper of the tapered ends 215a-b. Because the holding enclosure 210 is biased toward the receptive state, after the cylindrical trunk 106 is passed through the mouth 213 and into the holding enclosure 210, the holding enclosure 210 will return to its receptive state in which the width of the mouth 213 does not allow passage of the cylindrical trunk 106 without the sufficient force. Preferably, the force required to widen the mouth 213 is greater than gravity and/or the greatest force that will be experienced by moving the static trial holder 200 prior to placing the holding enclosure 210 in the contracted state. Therefore, once the cylindrical trunk 106 is in the holding enclosure 210, even before the holding enclosure 210 is placed in its contracted state, the cylindrical trunk 106 will not escape the holding enclosure 210 as the static trial holder 200 is oriented with the holding enclosure 210 downward, or is moved about.

It should be understood that when the static trial 100 (or distraction spacer) is being held (either when the holding enclosure 210 is in its receptive state or in its contracted state discussed below), because the semicylindrical extents 216a-b fit within the annular groove 104 of the static trial 100 (or distraction spacer), the static trial 100 (or distraction spacer) will not escape from the enclosure along the longitudinal axis of the cylindrical trunk 106. That is, as noted above, the recess 102 of each static trial 100 (or distraction spacer) forms an annular groove 104 that establishes the cylindrical trunk 106 between the baseplates of the static trial (or distraction spacer), such that the baseplates extend as flanges from either end of the cylindrical trunk 106. Accordingly, preferably, the opposing semicircular extents each have a thickness smaller than the width of the annular groove 104, and as such fit into the annular groove 104 to grip the cylindrical trunk 106 between them.

In some embodiments, while not shown in FIGS. 1a-f or FIGS. 2a-k, it is preferable that the annular groove 104 radially widen outwardly, such that the walls of the annular groove 104 taper toward one another with the increasing depth of the groove, such that the floor of the groove is more narrow than the opening 116 of the groove. Accordingly, preferably, in such embodiments, each semicircular extent 216a-b correspondingly radially widens outwardly, such that the thinner portion of the extent 216a-b fits closer to the floor of the annular groove 104, so that the tapered surfaces 215a-b of the extents 216a-b compress against the tapered walls of the annular groove 104 when the static trial 100 is gripped by the static trial holder 200. This taper locking provides for a secure grip so that the static trial 100 can be manipulated accurately and efficiently.

In some embodiments, while not shown in FIGS. 1a-f or FIGS. 2a-k, it is also preferable that the floor of the annular groove 104 of the cylindrical trunk 106 be ridged (e.g., have ridges that run parallel to the longitudinal axis of the cylindrical trunk), and the surfaces of the semicircular extents 216a-b of the static trial holder 200 that compress against the floor of the annular groove 104 when the static trial holder 200 grips the static trial 100 be correspondingly provided with ridges. The interlocking of the ridges of the static trial 100 with the ridges of the static trial holder 200 when the static trial 100 is gripped prevents rotation of the static trial 100 about the longitudinal axis of the cylindrical trunk 106 with respect to the static trial holder 200.

In order to more tightly hold the static trial 100 (or distraction spacer) for manipulation of the static trial 100 (or distraction spacer) during surgical procedures in which greater forces will be experienced by the static trial 100 (or distraction spacer) and the static trial holder 200, the holding enclosure 210 can be placed in a contracted state. The holding enclosure 210 can be considered "unlocked" in its receptive or expanded states, and "locked" in its contracted state, with respect to the nature of the hold that the static trial holder 200 potentially can have or has on the cylindrical trunk 106. Preferably, when the holding enclosure 210 is locked, a force greater than that which is applicable by an unaided surgeon or nurse (i.e., that which can be applied to remove the cylindrical trunk 106 from the holding enclosure 210 when the holding enclosure 210 is in its receptive state), and greater than that which will be experienced by the static trial 100 (or distraction spacer) and the static trial holder 200 during surgical procedures) would be required to pull the cylindrical trunk 106 out of the holding enclosure 210. The placement of the holding enclosure 210 in its locked state or unlocked state is effected by operation of a holding assembly that includes the extension 204 and the sleeve 206 and the manner in which they are configured and interact.

More particularly, the prongs 214a-b can be brought together, to lock the holding enclosure 210, by a rotation of the sleeve 206 with respect to the handle 202 and the extension 204 about the longitudinal axis of the shaft 208. A rotation control knob 219 is provided to ease the rotation of the sleeve 206. As shown in FIGS. 2g and 2i-j in view of FIGS. 2d-e, the bore 218 of the sleeve 206 (shown in cutaway in FIG. 2e) defines a cross-section that has a width 220 that is greater than its depth 222. Further as shown in those figures, the prongs 214a-b when separated (shown in cutaway in FIG. 2j) define a cross-section having a width 224 that is greater than its depth 226, the width 224 and depth 226 of the prong' cross-section being closely accommodated by the width 220 and depth 222 of the bore's cross-section. When the prongs 214a-b are together, the width of prongs' cross-section is closely accommodated by the depth 222 of the bore's cross-section. Thus, when the sleeve 206 is rotated with respect to the extension 204, the sides of the bore defining the depth 222 of its cross-section bear against the sides of the prongs 214a-b defining the width of their cross-section.

It should be noted that in order to ease the rotation of the sleeve 210 so that the side of the bore 218 can bear against the sides of the prongs 214a-b, the corners of the bore 218 are radiused, and at least the sides (that face away from one another) of the prongs 214a-b are curved. Preferably, as shown, the prongs 214a-b when separated define a partial cylindrical cross-section. The effect of the bearing (of the sides of the bore 218 against the sides of the prongs 214a-b) is borne by the space between the prongs 214a-b, so that the space narrows and the prongs 214a-b are brought toward one another until they are accommodated within the bore's depth 222. The bringing together of the prongs 214a-b brings the semicircular extents 216a-b together to place the holding enclosure 210 into its contracted state, locking it.

Preferably, the sleeve 206 is biased toward establishing the holding enclosure 210 in either an unlocked position or a locked position. Stated alternatively, when the holding enclosure 210 is unlocked (or locked), the force required to begin rotation of the sleeve 206 is greater than the force required to continue rotating the sleeve 206 once rotation has begun. And, as the sleeve 206 is rotated toward a position that will unlock (or lock), the holding enclosure 210, it is biased toward stopping its rotation at that upcoming position. Stated alternatively, as the sleeve 206 is being rotated, the force required to rotate the sleeve 206 past that upcoming position is greater than the force that is required to rotate it prior to reaching that upcoming position.

This biasing of the sleeve 206 toward positions that will either unlock or lock the holding enclosure 210 is effected by the inclusion of at least one spaced recess 228 on the outer surface of the extension 204, and at least one radial bore 230 through the wall of the sleeve 206 (preferably through the rotation control knob 219 as shown), which bores 230 each have secured therein a spring plunger (not shown) (it should be understood that functionally equivalent devices can also be used in place of a spring plunger). Preferably, each recess 228 is associated with a respective cooperating bore 230 and spring plunger. When a given bore 230 (and spring plunger) is aligned with its associated recess 228, the sleeve 206 is in a position at which the holding enclosure 210 is either unlocked or locked. Each of the spring plungers is biased radially inwardly from the inner surface of the sleeve 206, and as such presses against the outer surface of the extension 204 as the sleeve 206 is being rotated. Thus, when a recess 230 is presented to the spring plunger, it plunges into the recess 230, stopping the rotation of the sleeve 206. In order to restart (or continue) rotation of the sleeve 206, the bias of the spring plunger must be overcome when the restarting (or continuing) rotational force is applied. In order to lower the overcoming force required to restart or continue the rotation, the end of the spring plunger is preferably convexly curvate, and the recess is concavely curvate. Preferably, four recesses 228 and bores 230 (and spring plungers) are provided, each pair representing one of four quarter-turn rotated positions of the sleeve 206. At each position of the sleeve 206, all four plungers plunge into the recesses 228, securing the sleeve 206 at that position until a sufficient force is applied to overcome their plunging bias.

Accordingly, the static trials 100 of the invention (or distraction spacers such as those disclosed in the '127 application) can be held and manipulated with the static trial holder 200. Holding the handle 202 of the static trial holder 200 in one hand, an operator can push the cylindrical trunk 106 of the static trial 100 (or the distraction spacer) against the mouth 213 of the holding enclosure 210 with enough force to temporarily expand the mouth 213 to a width that will accommodate the diameter of the cylindrical trunk 106 for passage through the mouth 213. The radially inward tapering of the sides of the mouth 213 (the facing ends 215a-b of the semicircular extents 216a-b of the prongs 214a-b) facilitates this insertion. Once the cylindrical trunk 106 has passed into the holding enclosure 210, the operator can let go of the static trial 100 (or distraction spacer) because the prongs 214a-b will be overcome by their bias toward their neutral state and thus hold the static trial 100 in the holding enclosure 210 to prevent the static trial 100 from falling out or slipping out as the static trial holder 200 is moved with the static trial 100 prior to closing (e.g., locking) the holding enclosure 210. (When the static trial 100 (or distraction spacer) is being held in this manner, and the holding enclosure 210 is unlocked, the static trial 100 can be removed from the holding enclosure 210 by a pulling of the static trial 100 through the mouth 213 of the holding enclosure 210 with a force required to again temporarily overcome the bias of the prongs 214a-b toward their neutral state, to separate them and make the width of the mouth 213 accommodate the diameter of the cylindrical trunk 106.)

Once the operator is ready to lock the holding enclosure 210, while still gripping the handle 202 of the static trial holder 200, he rotates the rotation control knob 219 either clockwise or counterclockwise to move the sleeve 206 to the next quarter-turn position. If the rotation control knob 219 is rotated with enough force to cause the spring plungers in the bores 230 to back out of the recesses 228, the sleeve 206 will rotate as desired. Once the sleeve 206 has reached the next quarter-turn position, the spring plungers will find the recesses 228 associated with that position, and plunge into the recesses 228 to snap the sleeve 206 into the proper position. As the sleeve 206 rotates, the sides of the sleeve's bore's inner surface bear against the curved outer surfaces of the prongs 214a-b to push the prongs 214a-b together so that they are accommodated by the depth 222 of the bore 218. When the prongs 214a-b are pressed against one another and held in that closed position by the maintenance of the sleeve 206 in the new position (maintained by the spring plungers in the recesses 228), the semicircular extents 216a-b move toward one another and are correspondingly maintained together about the cylindrical trunk 106. When the prongs 214a-b are held in this manner, the cylindrical trunk 106 cannot be removed through the mouth 213 of the now-tighter (e.g., locked) holding enclosure 210 without the application of forces preferably greater than will be encountered when inserting and removing the static trial 100 from the intervertebral space during the surgical procedures. Once the static trial 100 has been inserted and removed from the intervertebral space (or the distraction spacer has been inserted and removed from the intervertebral space after being used to distract the space), the operator can lock the holding enclosure 210 by rotating the sleeve 206 another quarter turn (in either the clockwise or the counterclockwise direction). Again, if the rotation control knob 219 is rotated with enough force to cause the spring plungers to back out of the recesses 228, the sleeve 206 will rotate as desired. Once the sleeve 206 has reached the next quarter-turn position, the spring plungers will find the recesses 228 associated with that position, and plunge into the recesses 228 to snap the sleeve 206 into the proper position. As the sleeve 206 rotates, the sides of the sleeve's bore's inner surface move away from the curved outer surfaces of the prongs 214a-b and allow the prongs 214a-b to separate (under their own bias toward the neutral position) as they are accommodated by the width 220 of the bore 218. When the prongs 214a-b are separated and allowed to remain in that position by the maintenance of the sleeve 206 in the new position (maintained by the spring plungers in the recesses 228), the semicircular extents 216a-b are separated from one another and hold the cylindrical trunk 106 against falling or slipping out. That is, the cylindrical trunk 106 can be removed by the operator if the operator applies a sufficient force to widen the mouth 213 of the holding enclosure 210 enough to let the cylindrical trunk 106 pass through the mouth 213. Once the static trial 100 (or distraction spacer) is removed, another one can be inserted and manipulated if required.

Accordingly, the static trial holder 200 can be used to insert and remove the distraction spacers of the '127 application to distract the intervertebral space as described in the '127, and thereafter (or during the distraction) hold to insert and remove the static trials 100 to find the appropriate size of artificial intervertebral disc to be implanted.

A preferred embodiment of a dynamic trial of the present invention will now be described.

Referring now to FIGS. 3a-d, a dynamic trial of the present invention is shown in top (FIG. 3a), side (FIG. 3b), side cutaway (FIG. 3c) and perspective (FIG. 3d) views.

The dynamic trial 300 is provided primarily for distracting an intervertebral space according to the procedures described herein and/or for determining the appropriate size of an artificial intervertebral disc to be implanted (or whether a particular size can be implanted) into the distracted intervertebral space. While the distraction systems and methods described in the '127 application are also useful for distracting an intervertebral space, the dynamic trial 300 is provided as an additional or alternate distraction tool. Further, while the static trials described herein as useful for determining the appropriate size of an artificial intervertebral disc to be implanted (or whether a particular size can be implanted), the dynamic trial 300 is provided as an additional or alternate sizing tool.

More specifically, the dynamic trial 300 includes a shaft 302 having a bifurcated trial 304 at a distal end of the shaft 302. The trial 304 has an exterior that is preferably formed like the artificial intervertebral disc that it is meant to approximate. Accordingly, each half 306a-b of the bifurcated trial 304 has on its outwardly facing surface a convex dome 308a-b that is shaped like the convex dome of the corresponding baseplate of the artificial intervertebral disc that the dynamic trial 300 approximates (e.g., the convex domes 184a-b of the baseplates 168a-b of the artificial intervertebral disc 160 of FIGS. 1g-n). Preferably, each convex dome 308a-b is smooth, rather than having a porous coating that is preferred for the convex domes 184a-b of the artificial intervertebral disc 160, and each half 306a-b does not have stabilizing spikes such as the stabilizing spikes 188a-b on the outwardly facing surfaces 186a-b of the artificial intervertebral disc 160. The omission of these device stabilizing and bone ingrowth encouraging structures and surfaces on the dynamic trial 300 enables the surgeon to test the size of the artificial intervertebral disc 160 to be implanted without invading the vertebral body endplates. The shaft 302 includes an inner shaft portion 310 that centrally divides at a fulcrum 311 into upper and lower distal extensions 312a-b. The lower distal extension 312b is fixed to the upper distal extension 312a at the fulcrum 311, preferably by screws 313a-b that are plug welded in place. Preferably, as shown, at least the most proximal screw 313b extends above the top surface of the upper distal extension 312a to serve as a backup stop to prevent extreme forward movement of the control knob 318 that is operated to separate the distal extensions 312a-b (described below).

From the point of division to their distal ends, each of the upper and lower distal extensions 312a-b are spring biased (preferably by the formation of the fulcrum 311 in combination with the strength of the material of which the extensions 312a-b are made, although the use of other types of springs is contemplated by the present invention) toward positions in which they converge toward one another (in the figures, the extensions 312a-b are shown in these positions). The lower distal extension 312b is connected (preferably fixed as shown) to the lower half 306b of the bifurcated trial 304, and the upper distal extension 312a is connected to the upper half 306a of the bifurcated trial 304. Preferably, as shown, the upper half 306a is adjustably connected to the upper distal extension 312a by a pivot pin 315 that allows the upper half 306a to rotate about a lateral axis that passes through the longitudinal and lateral center of the bifurcated trial 304. This axis of rotation allows the upper half 306a, when separating from the lower half 306b, to adjust to the orientation of the upper (adjacent) vertebral bone without causing the bone to hinge relative to the lower vertebral bone (the bone adjacent the lower half 306b).

In order to effect the separation of the upper and lower halves 306a-b, the shaft 302 further includes an outer shaft potion 314 that is longitudinally translatable adjacent the inner shaft portion 310. The outer shaft portion 314 preferably straddles the inner shaft portion 310 as shown, and includes a pin 316 that passes between the distal extensions 312a-b. The outer shaft portion 314 is preferably translatable distally by the forward movement of a control knob 318 near the proximal end of the shaft 302, and translatable proximally by backward movement of the control knob 318. That is, when the control knob 318 is pushed distally, the outer shaft portion 314 is moves distally, and accordingly the pin 316 moves distally. If the pushing force is great enough to overcome the bias of the divided extensions 312a-b (their bias toward one another), the divided extensions 312a-b will separate as the pin 316 moves between them (to make room for the pin 316). The separation of the extensions 312a-b will correspondingly separate the halves 306a-b of the bifurcated trial 304. It should be understood that preferably, if the control knob 318 is released, the bias of the divided extensions 312a-b will press against the pin 316, causing the pin 316 (and correspondingly the outer shaft portion 314 and the control knob 318) to move proximally to allow the divided extensions 312a-b to return to their biased position, which will bring the halves 306a-b of the trial 304 back together so they can be removed from the intervertebral space. Preferably, markings 320 are provided on the inner shaft portion 310 (preferably on its top surface so that the surgeon can more easily see the markings 320) to quantify the depth (to which the bifurcated trial 304 is expanded) corresponding to the distance that the outer shaft portion 314 is translated with respect to the inner shaft portion 310.

It is anticipated that the pushing force required to separate the halves 306a-b will increase as they separate, due to the compression of the spine seeking to close the intervertebral space and the annulus seeking to prevent the adjacent vertebral discs from separating beyond a certain point. Therefore, to provide a mechanical advantage to the operator in the event that greater distraction is required, but the operator cannot push the control knob 318 farther with unaided human effort, an fine control knob 322 is provided. The fine control knob 322 is preferably threaded onto the proximal end of the inner shaft portion 310, proximal to the control knob 318. Thus, rotation of the fine control knob 322 about the longitudinal axis of the inner shaft portion 310 will cause the body of the fine control knob 322 to press against the control knob 318 to move it farther distally. The interference of the threads of the fine control knob-inner shaft portion interface prevents the fine control knob 322 from backing up proximally unless the fine control knob 322 is reverse rotated to effect that result.

Preferably, as shown, the proximal end 324 of the shaft 302 is preferably flanged to serve as a slap hammer for impaction (by hitting the proximal end 324 with a mallet with a distally directed force, e.g.), if necessary for proper positioning of the bifurcated trial 304, and/or forced extraction of the bifurcated trial 304 (by hitting the flange of the proximal end 324 with a mallet with a proximally directed force, e.g.).

Accordingly, the dynamic trial 300 can be used as an additional or alternative distracting tool (e.g., to the distraction spacers), and/or as an alternative or additional sizing tool (e.g., to the static trials). As an example of a use for the dynamic trial 300 as an alternative or additional distraction tool and an alterative sizing tool, once the intervertebral space is distracted to (or, without distraction, is at) a depth that is at least equal to the depth of the closed bifurcated trial 304, the bifurcated trial 304 of the dynamic trial 300 can be inserted into the intervertebral space. (If the intervertebral space must be distracted initially because it starts out more shallow than the depth of the closed bifurcated trial 304, the distraction spacers of the '127 application and the methods disclosed therein can be used, e.g.) The control knob 318 and/or fine control knob 322 can be operated to separate the halves 306a-b of the bifurcated trial 304 to distract the space as clinically appropriate. Because the bifurcated trial 304 is shaped externally to approximate the artificial intervertebral disc to be implanted (e.g., the artificial intervertebral disc 160), and because the pivoting of the upper half 306a of the bifurcated trial 304 allows the halves 306a-b to appropriately lordotically orient themselves, when the surgeon determines the intervertebral space to be distracted to its proper dimension (based on how much compression is being experienced on the dynamic trial 300 and how tight the annulus is), he can read the markings 320 on the shaft 302 to determine what size of artificial intervertebral disc 160 is suitable for the dimensioned intervertebral space. A subsequent bringing together of the halves 306a-b and a removal of the dynamic trial 300 can then be followed by insertion of the appropriately sized artificial intervertebral disc 160 (e.g., in a manner described below with regard to the inserter/impactor 400).

As an example of a use for the dynamic trial 300 as an alternative distraction tool and an additional sizing tool, after the surgeon has initially distracted the intervertebral space (preferably with the distraction spacers of the '127 application), and applied one or more of the static trials 100 to the intervertebral space to determine the appropriate size of the artificial intervertebral disc to be implanted (e.g., the artificial intervertebral disc 160), the surgeon can apply the dynamic trial 300, expand it to the size of the static trial 100 that was determined to be the appropriate size for the intervertebral space, and then further open the dynamic trial 300 for a final sizing. An example of a final sizing that would be useful would be to test the amount of farther distraction that is clinically possible, without having to remove and replace static trials 100 when the compression force of the spine and the tension force of the annulus are at their higher levels. Also, the surgeon may wish to distract the space slightly more than the size of the appropriately sized static trial 100 or artificial intervertebral disc 160, so that the artificial intervertebral disc 160 can be more easily inserted after removal of the static 100 or dynamic trial 300 results in a compressive settling of the intervertebral space. The surgeon may also wish to distract the space slightly more than the size of the appropriately sized static trial 100 or artificial intervertebral disc 160, to prepare it for easy insertion of the artificial intervertebral disc 160 to be implanted, with consideration for the height of the stabilizing spikes 188a-b on the outwardly facing surfaces 186a-b of the baseplates 168a-b of the artificial intervertebral disc 160. While the artificial intervertebral disc 160 having the spikes 188a-b can be implanted without the additional distraction, some surgeons may find such additional distraction useful or desirable for a particular case.

A preferred embodiment of an inserter/impactor of the present invention will now be described.

Referring now to FIGS. 4a-d, an inserter/impactor of the present invention is shown in side (FIG. 4a), top (FIG. 4b), side cutaway (FIG. 4c) and perspective (FIG. 4d) views. FIGS. 4e-h show side (FIG. 4e), top (FIG. 4i), side cutaway (FIG. 4g), and perspective (FIG. 4h) views of an inserter/impactor of the present invention holding a static trial of the present invention. FIGS. 4i-j show top views of an inserter/impactor of the present invention holding a static trial of the present invention in two alternative ways. FIGS. 4k-n show side (FIG. 4k), top (FIG. 4l), side cutaway (FIG. 4m), and perspective (FIG. 4n) views of an inserter/impactor of the present invention holding an exemplary artificial intervertebral disc of the present invention. FIGS. 4o-p show top views of an inserter/impactor of the present invention holding an exemplary artificial intervertebral disc of the present invention in two alternative ways.

The inserter/impactor 400 is provided primarily for holding, inserting, repositioning, removing, impacting, extracting, and otherwise manipulating an artificial intervertebral disc having features suitable for being manipulated by the inserter/impactor. (However, it can also be used to hold, insert, reposition, remove, impact, extract, and otherwise manipulate the static trials 100 as described above, as well as any other orthopedic device having suitable features therefor.) Exemplary suitable artificial intervertebral discs include, but are not limited to, the artificial intervertebral disc 160 described herein and the artificial intervertebral discs described in the '160 application with regard to FIGS. 8a-y, 9a-t, 10a-t, 11a-j, and 12a-o thereof and by the accompanying descriptions therefor (e.g., embodiments identified as the first, second, third, fourth, and fifth preferred embodiments of the fourth embodiment family, etc.). Regarding the features suitable for being manipulated by the inserter/impactor 400, such features include those discussed above as being suitable features on the static trials 100 and disc 160, namely, an anteriorly facing flat surface on the second (e.g., lower) baseplate of the trial or disc, flanked by two anteriolaterally facing flat surfaces (one on each side of the anteriorly facing flat surface), and, to provide for holding of the trial or disc for an anterior insertion approach, a hole spaced from the anteriorly facing flat surface, the hole having a longitudinal axis parallel to the anteriorly facing flat surface.

More particularly, the inserter/impactor 400 includes a shaft 402 having a distal end 404 that has angled flat surfaces 420*a-c* corresponding to and fittable against angled flat surfaces of the static trial (e.g., the surfaces 120*a-c* of the static trial 100) or artificial intervertebral disc (e.g., the surfaces 180*a-c* of the artificial intervertebral disc 160) to be implanted. For example, in an anterior approach for the trial 100 (as shown in FIGS. 4*e-h*), 120*a* and 120*d* facing 420*a*, 120*b* and 120*e* facing 420*b*, and 120*c* and 120*f* facing 420*c*, and in an anterior approach for the disc 160 (as shown in FIGS. 4*k-n*), 180*a* and 180*d* facing 420*a*, 180*b* and 180*e* facing 420*b*, and 180*c* and 180*f* facing 420*c*.

Further, the inserter/impactor 400 includes a holding pin 408 that extends from the center flat surface 420*b* along a longitudinal axis of the shaft 402, the pin 408 having a distal end 410 that bends downward. The holding pin 408 is spring loaded (by a spring 409) in a central channel of the shaft 402, so that it is biased toward and against the central flat surface 420*b* (preferably, the bent end 410 of the pin 408 prevents it from entering the central channel).

A flange 411, mechanically connected to the pin 408 and translating adjacent the shaft 402, can be pushed distally to overcome the bias of the spring 409 to space the pin 408 away from the central flat surface 420*b*. In this position, the pin 408 can be inserted in the hole 120*b*, 180*b* in the baseplate 108*b*, 168*b* of the static trial 100 or artificial intervertebral disc 160. Releasing the flange 411 allows the spring 409 to pull the pin 408 back, causing the anteriorly facing surface 120*b*, 180*b* of the baseplate 108*b*168*b* to be held against the central flat surface 420*b* of the inserter/impactor 400 and the anterioloaterally facing flat surfaces 120*a,c*,180*a,c* of the static trial 100 or artificial intervertebral disc 160 to be held against the other corresponding flat surfaces 420*a,c* of the inserter/impactor 400. A knob 412, threaded on the shaft 402, can be rotated about the longitudinal axis of the shaft 402 to push the flange 411 farther proximally, to pull the pin 409 tighter and therefore lock its position (the interference of the threads of the knob-shaft interface prevents the knob 412 from moving distally unless the knob 412 is reverse rotated to effect that result) to more securely hold the baseplate 108*b*,168*b*, and reverse rotated to unlock and loosen the pin 409.

When the static trial 100 or disc 160 is held in this manner, rotation of the static trial 100 or disc 160 about a longitudinal axis (of the static trial 100 or disc 160) relative to the inserter/impactor 400 is prevented by interference of the corners of the static trial's 100 or disc's 160 flat surfaces 120*a-c*,180*a-c* and the corners of the inserter/impactor's 400 flat surfaces 420*a-c*, similar to the manner in which a wrench holding a nut prevents rotation of the nut relative to the wrench. Further, the holding of the static trial 100 or disc 160 in this manner allows for some repositioning of the static trial 100 or disc 160 in the intervertebral space via rotation of the static trial 100 or disc 160 in either direction about the longitudinal axis of the intervertebral space.

Preferably, both of the baseplates of the static trial 100 or disc 160 have similarly configured flat surfaces. For example, the lower baseplate's 108*b*,168*b* flat surfaces 120*a-c*,180*a-c* have similarly configured and similarly oriented counterpart flat surfaces 120*d-f*,180*d-f* on the upper baseplate 108*a*, 168*a*. Further preferably, both baseplates' 108*a-b*,168*a-b* flat surfaces 120*a-f*,180*a-f* face the angled flat surfaces 420*a-c* of the inserter/impactor 400 when the static trial 100 or disc 160 is held by the inserter/impactor 400. For example, in an anterior approach for the trial 100 (as shown in FIGS. 4*e-h*), 120*a* and 120*d* facing 420*a*, 120*b* and 120*e* facing 420*b*, and 120*c* and 120*f* facing 420*c*, and in an anterior approach for the disc 160 (as shown in FIGS. 4*k-n*), 180*a* and 180*d* facing 420*a*, 180*b* and 180*e* facing 420*b*, and 180*c* and 180*f* facing 420*c*.

It should be noted that preferably, when the static trial 100 is held by the inserter/impactor 400, the flat surfaces 120*a-c* and the counterpart flat surfaces 120*d-f* are tightly held against the angled flat surfaces 420*a-c* of the inserter/impactor 400 as described above. It is also preferable that the baseplates 108*a-b* of each of the plurality of static trials 100 be appropriately lordotically angled relative to one another to ease insertion of the static trial 100 into the intervertebral space and to mimic how the artificial intervertebral disc 160 will typically be oriented as it is being inserted using the inserter/impactor 400, and to ease insertion of the static trial 100 into the intervertebral space. While not shown in FIGS. 1*a-f*, in some embodiments, when the static trials 100 are formed in such a lordotically oriented configuration, it is preferable that the flat surfaces 120*d-f* on the first (e.g., upper) baseplate 108*a* be parallel to the flat surfaces 120*a-c* of the second (e.g., lower) baseplate 108*b* in the static trial's 100 appropriately lordotically oriented configuration, so that when the static trial 100 is held tightly by the inserter/impactor 400, the flat surfaces 120*a-f* are flush with the flat surfaces 420*a-c* of the inserter/impactor 400 even though the baseplates 108*a-b* are lordotically angled with respect to one another.

By contrast, preferably, when the artificial intervertebral disc 160 is held by the inserter/impactor 400, the flat surfaces 180*a-c* are tightly held against the angled flat surfaces 420*a-c* of the inserter/impactor 400 as described above, but the counterpart flat surfaces 180*d-f* are loosely held against the angled flat surfaces 420*a-c* of the inserter/impactor 400. As such, the structure of the artificial intervertebral disc 160 having the counterpart flat surfaces 180*d-f* (e.g., the upper baseplate 168*a*) is able to angulate and rotate to a limited extent relative to the structure of the artificial intervertebral disc 160 having the flat surfaces 180*a-c*. This permits the artificial intervertebral disc 160 to adjust to the intervertebral space (e.g., to the angulation of the adjacent vertebral endplates, defining the intervertebral space, relative to one another) as it is being inserted thereinto. That is, typically, the adjacent vertebral endplates will be lordotically angled with respect to one another as a result of the intervertebral space being prepared and distracted. As the artificial intervertebral disc 160 is then inserted into the intervertebral space using the inserter/impactor 400, then, the baseplates 168*a-b* will be permitted to lordotically angle with respect to one another to squeeze into the intervertebral space.

Also preferably, in order to provide for a holding of the static trial 100 or disc 160 for two additional (here, anteriolateral) insertion approaches, each static trial 100 or disc 160 also includes two additional holes 122*a*,182*a* and 122*c*,182*c*, one (e.g., 122*a*,182*a*) spaced apart from one of the anteriolaterally facing flat surfaces (e.g., 120*a*,180*a*), and the other (e.g., 122*c*,182*c*) spaced apart from the other of the anteriolaterally facing flat surfaces (e.g., 120*c*,180*c*). Accordingly, operation of the inserter/impactor 400 can fit the holding pin 408 into either of these two additional holes 122a,182a or 122c,182c, and hold the associated anteriolaterally facing flat surface (the one associated with the hole into which the pin 408 is fit) of the static trial 100 or disc 160 against the flat surface of the inserter/impactor 400 opposite the pin 408. For example, as discussed below with regard to the inserter/impactor 400, in a first anteriolateral approach for the trial 100 (as shown in FIG. 4i), 120a and 120d facing 420b, 120b and 120e not confronted, and 120c and 120f facing 420a, and a first anteriolateral approach for the disc 160 (as shown in FIG. 4o), 180a and 180d facing 420b, 180b and 180e not confronted, 180c and 180f facing 420a. And, for example, as discussed below with regard to the inserter/impactor 400, in a second anteriolateral approach for the trial 100 (as shown in FIG. 4j), 120a and 120d facing 420c, 120b and 120e facing 420a, and 120c and 120f not confronted, and a second anteriolateral approach for the disc 160 (as shown in FIG. 4p), 180a and 180d facing 420c, 180b and 180e facing 420a, 180c and 180f not confronted.

It should be understood that preferably, in order to facilitate these additional approaches, the angle separating the anteriorly facing flat surface of the static trial 100 or disc 160 and one of the anteriolaterally facing flat surfaces of the static trial 100 or disc 160 is equal to the angle separating the anteriorly facing flat surface and the other of the anteriolaterally facing flat surfaces. Preferably, the surfaces are angled with respect to one another at an angle of 33.4 degrees.

It should also be understood that the inclusion of additional adjacent angulated surfaces (or placing the angulated surfaces in other locations on the trial or disc), and/or including corresponding holes adjacent to such surfaces, can provide the surgeon with additional approaches, e.g., other anteriolateral approaches, directly lateral approaches, posteriolateral approaches, and/or directly posterior approaches. For example, a trial or disc can have angled surfaces (and corresponding holes) along the entire perimeter of one or both of the baseplates, and thus enable the surgeon to engage the trial or disc from a number of angles, including anterior, posterior, lateral, anteriolateral, and posteriolateral angles.

The inserter/impactor 400 further includes at a proximal end a cap 414 for use as an impact surface if the trial 100 or disc 160 must be impacted further into the intervertebral space after insertion, or forcibly extracted from the intervertebral space. A mallet can be used to strike the cap 414 (in a distal direction for impaction, or in a proximal direction (using the flange of the cap 414) for extraction). It should be noted a striking of the cap 414 will translate the striking force to the baseplates through the shaft 402 and the flat surfaces, but will not damage the holding pin 408 because the holding pin 408 is spring loaded in the central channel and thus buffered from the striking force thereby.

Accordingly, the inserter/impactor 300 can be used to grip either the static trials or the artificial intervertebral disc to be implanted, and hold the same during insertion and/or removal of the same, and is useful for, a variety of surgical approach angles.

Preferred embodiments of a repositioner/extractor of the present invention will now be described.

Figure 5A:
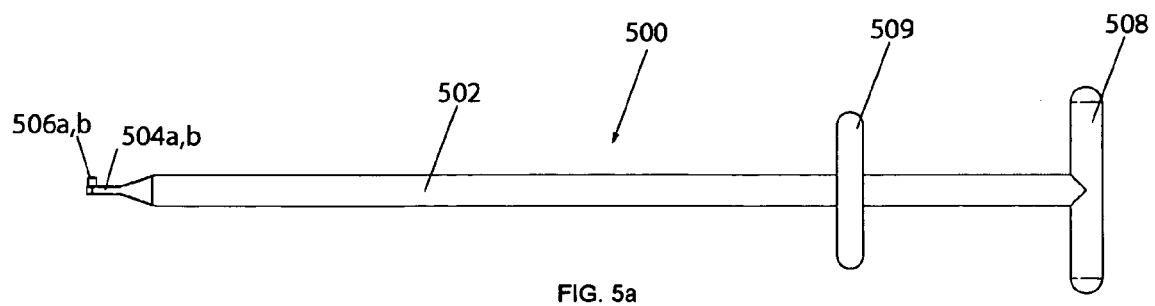
FIGS. 5a-c show side (FIG. 5a), top (FIG. 5b), and perspective (FIG. 5c) views of a symmetric repositioner/extractor of the present invention.
Figure 5B:
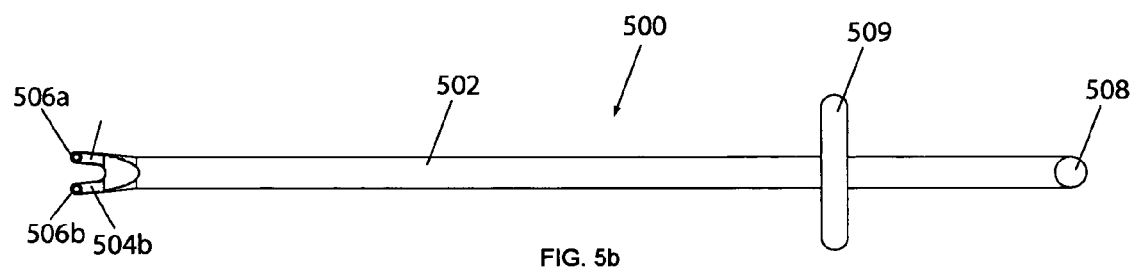
Figure 5C:
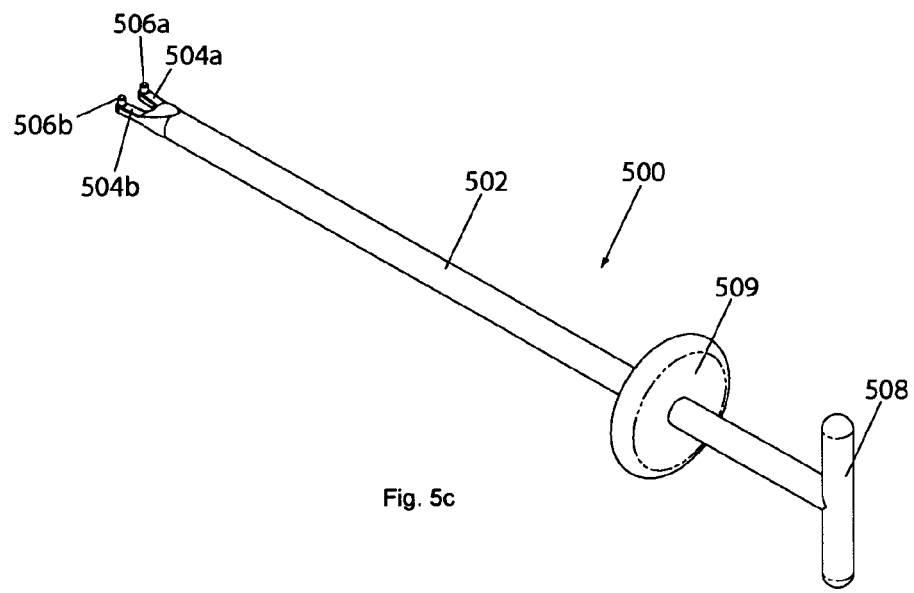
Figure 5D:
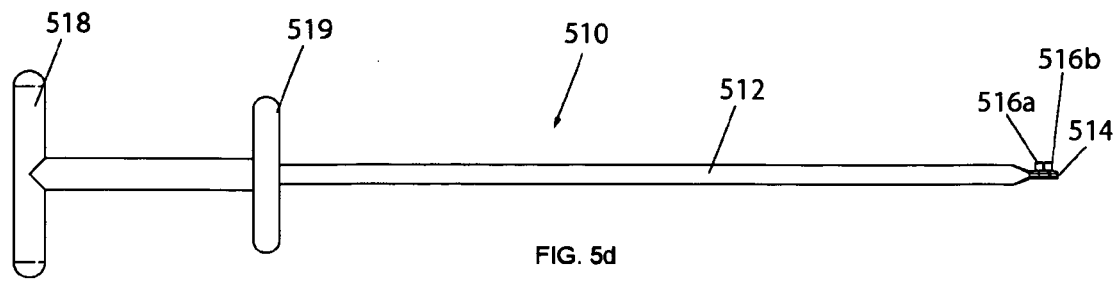
FIGS. 5d-f show side (FIG. 5d), top (FIG. 5e), and perspective (FIG. 5f) views of an offset left repositioner/extractor of the present invention.
Figure 5E:
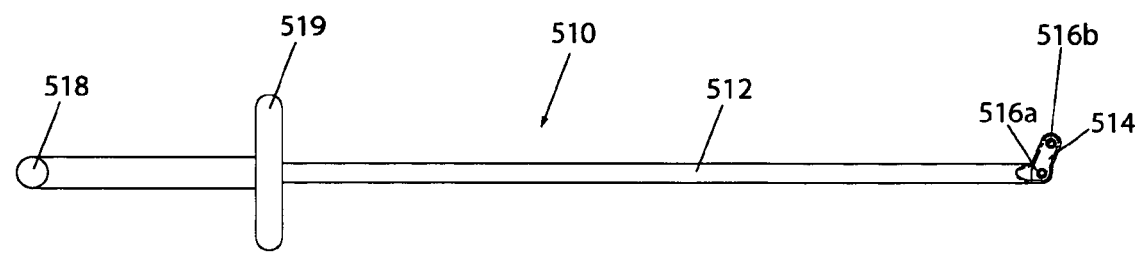
Figure 5F:
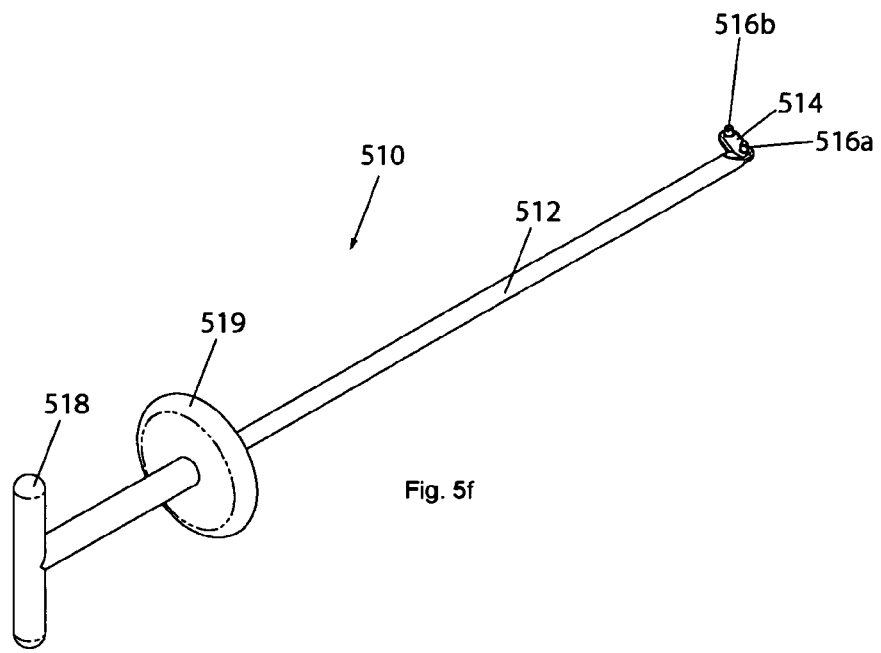
Figure 5G:
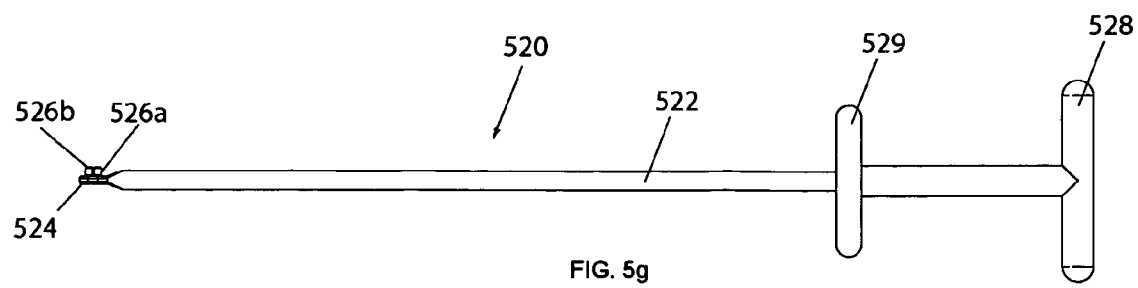
FIGS. 5g-i show side (FIG. 5g), top (FIG. 5h), and perspective (FIG. 5i) views of an offset right repositioner/extractor of the present invention.
Figure 5H:
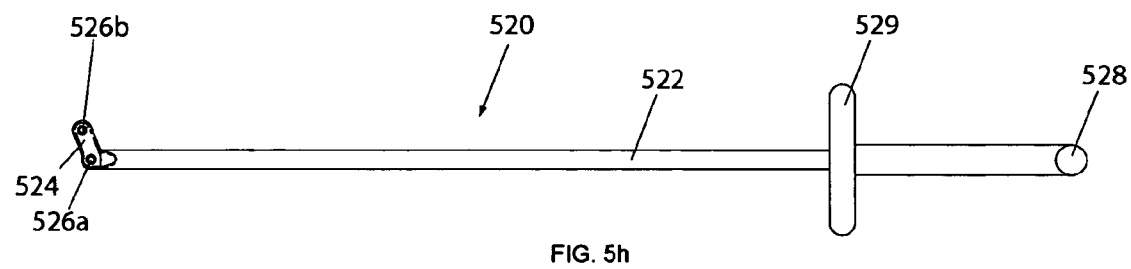
Figure 5I:
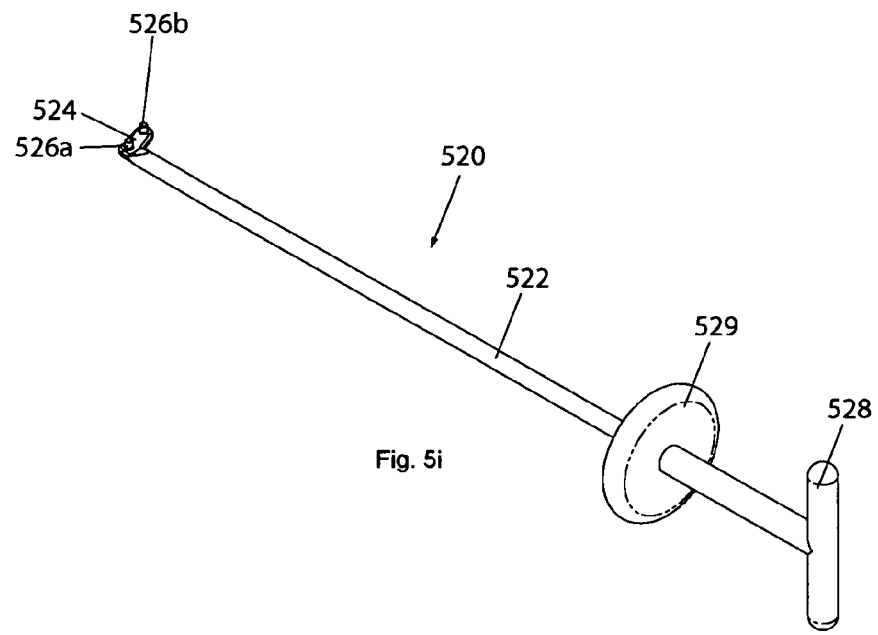
Figure 5J:
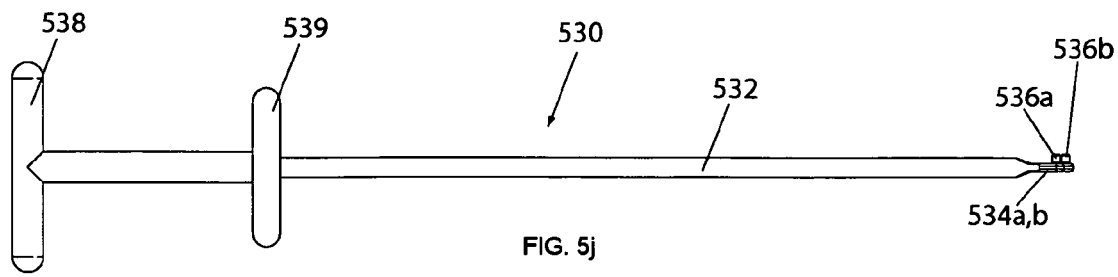
FIGS. 5j-l show side (FIG. 5j), top (FIG. 5k), and perspective (FIG. 5l) views of an alternative offset left repositioner/extractor of the present invention.
Figure 5K:
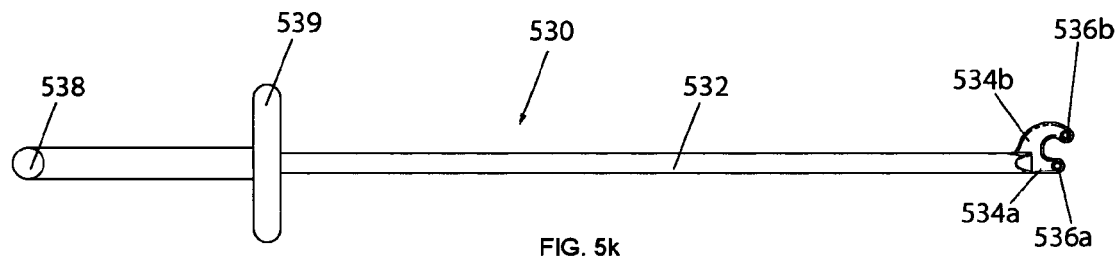
Figure 5L:
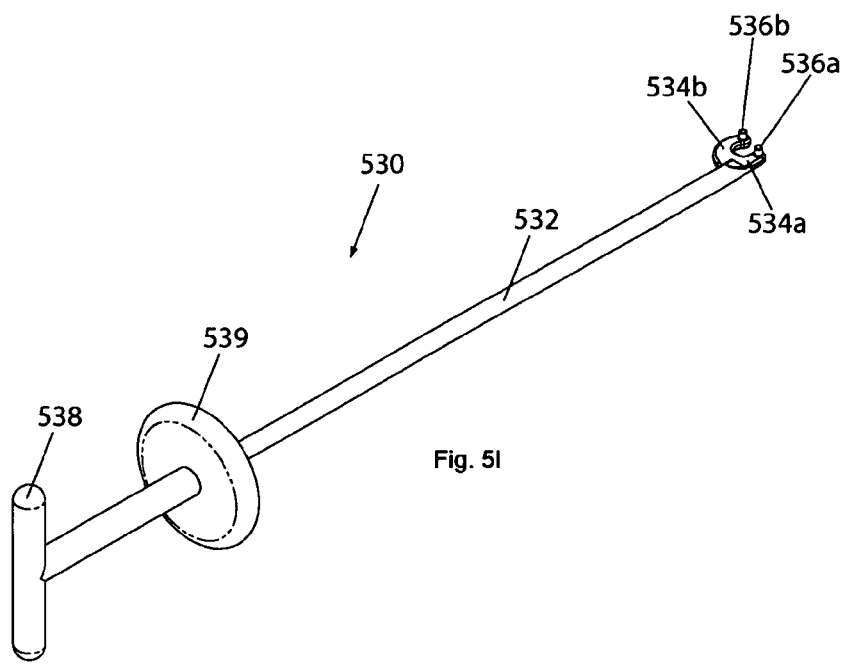
Figure 5M:
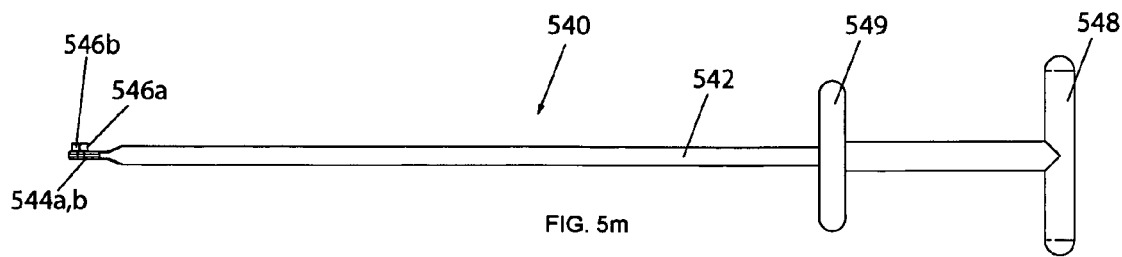
FIGS. 5m-o show side (FIG. 5m), top (FIG. 5n), and perspective (FIG. 5o) views of an alternative offset right repositioner/extractor of the present invention.
Figure 5N:
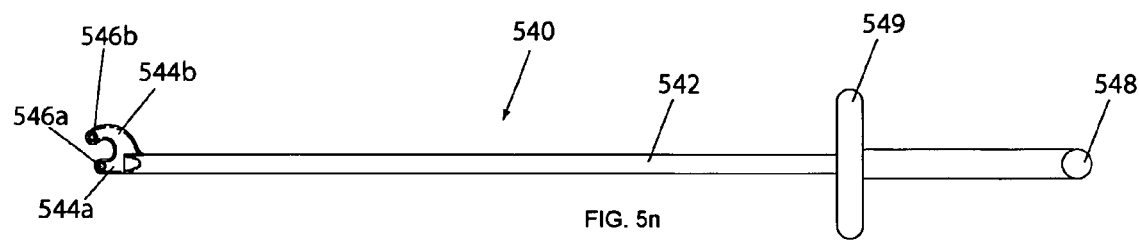
Figure 5O:
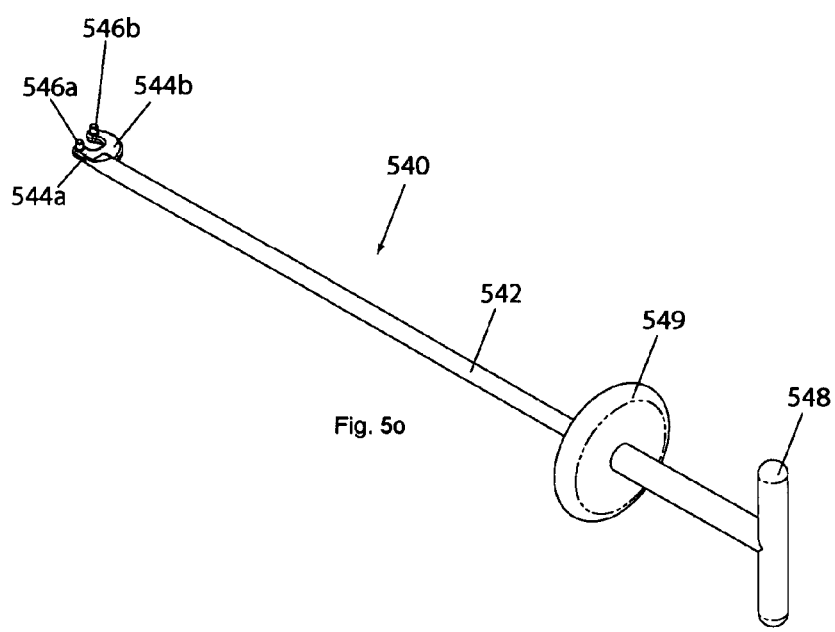

Referring now to FIGS. 5a-c, a symmetric repositioner/extractor of the present invention is shown in side (FIG. 5a), top (FIG. 5b), and perspective (FIG. 5c) views. And referring now to FIGS. 5d-f, an offset left repositioner/extractor of the present invention is shown in side (FIG. 5d), top (FIG. 5e), and perspective (FIG. 5f) views. And referring now to FIGS. 5g-i, an offset right repositioner/extractor of the present invention is shown in side (FIG. 5g), top (FIG. 5h), and perspective (FIG. 5i) views. And referring now to FIGS. 5j-l, an alternative offset left repositioner/extractor of the present invention is shown in side (FIG. 5j), top (FIG. 5k), and perspective (FIG. 5l) views. And referring now to FIGS. 5m-o, an alternative offset right repositioner/extractor of the present invention is shown in side (FIG. 5m), top (FIG. 5n), and perspective (FIG. 5o) views.

Each repositioner/extractor is provided primarily for repositioning and/or extracting a static trial or artificial intervertebral disc having features suitable for being manipulated by the repositioner/extractor. Exemplary suitable artificial intervertebral discs are described in the '160 application with regard to FIGS. 8a-y, 9a-t, 10a-t, 11a-j, and 12a-o thereof and by the accompanying descriptions therefor (e.g., embodiments identified as the first, second, third, fourth, and fifth preferred embodiments of the fourth embodiment family, etc.). Regarding the features suitable for being manipulated by each repositioner/extractor, such features include at least two holes extending longitudinally into one of the baseplates of the static trial or artificial intervertebral disc from the inwardly facing surface of the baseplate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

In order to engage the two holes, each repositioner/extractor has two pins extending in parallel from a central shaft, perpendicular to the longitudinal axis of the central shaft. The pins are spaced to engage the two holes simultaneously, and each pin has a diameter smaller than the diameter of the hole it is to engage. Therefore, the pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating of the central shaft of the repositioner/extractor about its distal end, about an axis parallel to the longitudinal axes of the pins. A handle at a proximal end of the central shaft is useful for pushing or pulling on the shaft. A flange adjacent the proximal end of the shaft is useful for impaction (either with a distally directed force or a proximally directed force), if necessary to manipulate the shaft.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles.

For example, three repositioner/extractors are illustrated, and, for example, two hole configurations are illustrated.

The first, symmetric, repositioner/extractor 500, shown in FIGS. 5a-c, includes a shaft 502 having a distal end that is symmetrically divided into two prongs 504a-b, each of the prongs having a pin 506a-b extending upwardly and parallel to the pin on the other prong. The second and third, left offset and right offset, repositioners/extractors 510,520, shown in FIGS. 5*d-f* and 5*g-i*, respectively, each include a shaft 512, 522 having a distal end that bends diagonally laterally, the left offset distal end 514 bending in one direction (e.g., to the left), the right offset distal end 524 bending in an opposite direction (e.g., to the right). The distal end of each of the second and third repositioners/extractors 510,520 has two pins 516*a-b*, 526*a-b* serially spaced on the bent portion, and each of the pins extends upwardly and parallel to the other pin. (As shown in FIGS. 5*j-l* and 5*m-o*, alternative embodiments 530, 540 of the second and third, left offset and right offset, repositioners/extractors each include a shaft 532,542 having a distal end that has a straight prong 534*a*,544*a* and a curved lateral prong 534*b*,544*b*, where the curved lateral prong 534*b* extends in one direction (e.g., left) for the alternative left offset repositioner/extractor 530, and where the curved lateral prong 544*b* extends in an opposite direction (e.g., right) for the alternative right offset repositioner/extractor 540. Each of the prongs 534*a-b*,544*a-b* has a pin 536*a-b*,546*a-b* extending upwardly and parallel to the pin on the other prong. The alternative repositioners/extractors 530,540, each having a space between the pins 536*a,b*,546*a,b*, provides for avoidance of any structures on the static trial or artificial intervertebral disc that may be present between the holes.) On each of the repositioners/extractors 500, 510, 520, 530, 540, the pins are spaced so that they simultaneously each fit into a respective one of the two adjacent holes in the baseplate of the static trial or artificial intervertebral disc. Each of the repositioners/extractors 500, 510, 520, 530, 540 has a handle 508, 518, 528, 538, 548 at a proximal end of the central shaft which is useful for pushing or pulling on the shaft, and a flange 509, 519, 529, 539, 549 adjacent the proximal end of the shaft that is useful for impaction (either with a distally directed force or a proximally directed force), if necessary to manipulate the shaft.

As noted above, the repositioner/extractor that is appropriate or desired for a given case depends at least in part on the configuration of the holes in the baseplates. Two hole configurations are disclosed, as examples of suitable configurations, although other configurations are possible and contemplated by the present invention. A first hole configuration includes three holes on one of the baseplates, the holes being configured so that a first hole is located in the anterior-posterior plane, and the adjacent (second and third) holes are located in respective opposing anteriolateral planes on either side of the first hole. This hole configuration is shown in FIGS. 5*p-u*, each of which shows a top cutaway view of the artificial intervertebral disc of FIGS. 1*g-n*, showing its lower baseplate, having the first hole configuration, engaged by one of the repositioners/extractors 500,510,520. Each view of the lower baseplate shows the first hole 550, the second hole 552, and the third hole 554 of the first hole configuration.

A second hole configuration includes four holes on one of the baseplates, the holes being configured so that first and second holes straddle the anterior-posterior plane, a third hole is located so that the third hole and the first hole straddle one of the opposing anteriolateral planes, and a fourth hole is located so that the fourth hole and the second hole straddle the other of the opposing anteriolateral planes. This hole configuration is shown in FIGS. 5*v-dd*, each of which shows a bottom cutaway view of the artificial intervertebral disc of FIGS. 1*g-n*, showing its upper baseplate, having the second hole configuration, engaged by one of the repositioners/extractors 500,510,520. Each view of the upper baseplate shows the first hole 560, the second hole 562, the third hole 564, and the fourth hole 566, of the second hole configuration.

It should be understood that configurations having more or fewer holes, and in a variety of locations, are contemplated by the invention, and the detailed descriptions of only two hole configurations is not meant to limit the invention to only these two configurations. Importantly, the invention encompasses using a hole or any number of holes, bored at any suitable angle, whether parallel to other holes or not, in any number of locations on a spacer, a trial or an artificial intervertebral disc (not limited to locations on the baseplates), for purposes of enabling the spacer, trial, or disc to be gripped by a manipulation instrument (not limited to a repositioner/extractor) that engages the hole, and/or to enable the surgeon to work from a variety of approaches. For example, as described in more detail below, the first and second hole configurations described herein, in cooperation with the repositioner/extractors, provide the surgeon with the ability to work from a directly anterior approach, as well as several anteriolateral approaches. It should be understood that additional hole configurations can enable the surgeon to work from a directly posterior approach, posteriolateral approaches, directly lateral approaches, or anteriolateral approaches that are different that those illustrated. For example, the placement of one or more suitably spaced holes (or the addition of one or more holes) on the posterior edge, and/or one or both of the lateral edges of one or both of the baseplates, would enable the surgeon to use the repositioner/extractors of the present invention to achieve such approaches.

As noted above, and referring now to FIGS. 5*p-dd*, it can be seen that each of the repositioner/extractors can be used in more than one manner depending on the tool desired and the approach desired. For example, with reference to FIGS. 5*p-q*, regarding the first hole configuration (three holes in one of the baseplates), the symmetric repositioner/extractor 500 can be used in either of two anteriolateral approaches (see FIGS. 5*p-q*). That is, the symmetric repositioner/extractor's shaft 502 can be inserted into the wound from either of the two anteriolateral approaches, and the pins 506*a-b* can be inserted into the first 550 and second 552 holes (for one of the two anteriolateral approaches) (FIG. 5*p*) or the first 550 and third 552 holes (for the other of the two anteriolateral approaches) (FIG. 5*q*) of the first hole configuration.

Figure 5P:
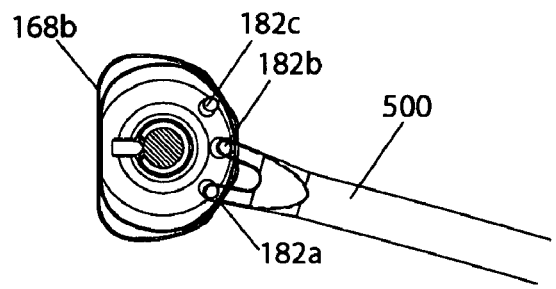
FIGS. 5p-u show exemplary various possible repositioner/extractor approach angles with a three hole configuration of the present invention.
Figure 5Q:
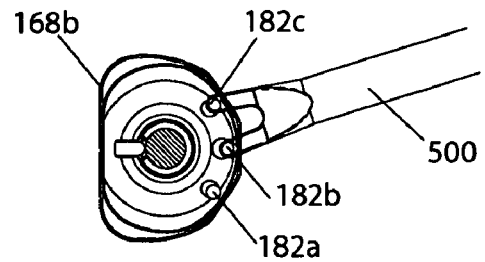
Figure 5R:
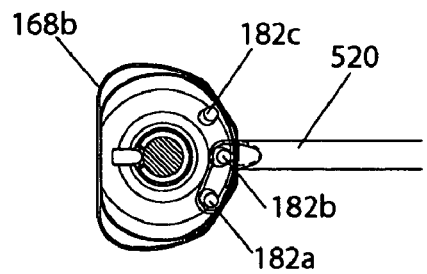
Figure 5S:
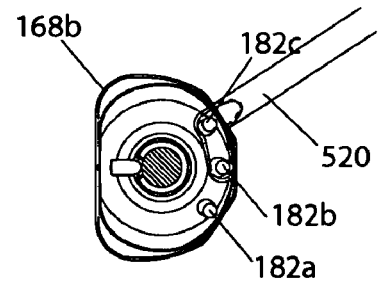
Figure 5T:
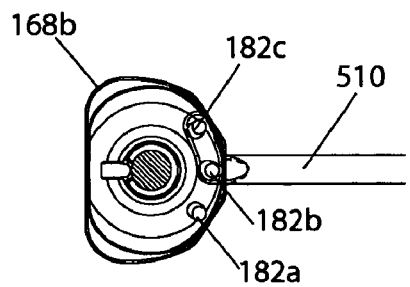
Figure 5U:
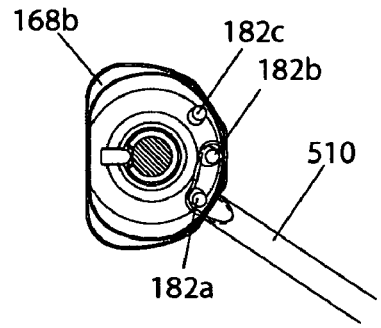

Also, for example, with reference to FIGS. 5*r-u*, regarding the first hole configuration, each of the left offset repositioner/extractor 510 and the right offset repositioner/extractor 520 can be used in either a directly anterior approach (FIGS. 5*r,t*) or a respective anteriolateral approach (FIGS. 5*s,u*). That is, the right offset repositioner/extractor's shaft 522 can be inserted into the wound from a direct anterior approach, and the right offset repositioner/extractor's pins 526*a-b* can then be placed into the first 550 and second 552 holes of the first hole configuration (FIG. 5*r*). And, the right offset repositioner/extractor's shaft 522 can be inserted into the wound from an anteriolateral approach, and the right offset repositioner/extractor's pins 526*a-b* can then be placed into the first 550 and third 554 holes of the first hole configuration (FIG. 5*s*). And, the left offset repositioner/extractor's shaft 512 can be inserted into the wound from a direct anterior approach, and the left offset repositioner/extractor's pins 516*a-b* can then be placed into the first 550 and third 554 holes of the first hole configuration (FIG. 5*t*). And, the left offset repositioner/extractor's shaft 512 can be inserted into the wound from an anteriolateral approach, and the left offset repositioner/extractor's pins 516*a-b* can then be placed into the first 550 and second 552 holes of the first hole configuration (FIG. 5*u*). It should be noted that the alternate left offset 530 and alternate right offset 540 repositioners/extractors can also fit into the holes of the first hole configuration in the same manner as described here with regard to the left offset 510 and right offset 520 repositioners/extractors.

Also, for example, with reference to FIGS. 5*v*-*dd*, regarding the second hole configuration (four holes in one of the baseplates), the symmetric repositioner/extractor 500 can be used in a directly anterior approach (FIG. 5*v*), and either of two anteriolateral approaches (FIGS. 5*w*-*x*). That is, the symmetric repositioner/extractor's shaft 502 can be inserted into the wound from a directly anterior approach, and the pins 506*a*-*b* can be inserted into the first 560 and second 562 holes of the second hole configuration (FIG. 5*v*). And, the symmetric repositioner/extractor's shaft 502 can be inserted into the wound from either of the two anteriolateral approaches, and the pins 506*a*-*b* can be inserted into the first 560 and third 564 holes (for one of the two anteriolateral approaches) (FIG. 5*w*) or the second 562 and fourth 566 holes (for the other of the two anteriolateral approaches) (FIG. 5*x*) of the second hole configuration.

Also, for example, with reference to FIGS. 5*y*-*dd*, regarding the second hole configuration, each of the left offset repositioner/extractor 510 and the right offset repositioner/extractor 520 can be used in any of three respective anteriolateral approaches. That is, the right offset repositioner/extractor's shaft 522 can be inserted into the wound from any of its three possible anteriolateral approaches, and the right offset repositioner/extractor's pins 526*a*-*b* can then be placed into the first 560 and second 562 holes (FIG. 5*y*) (for a first of the three anteriolateral approaches), the first 560 and third 564 holes (FIG. 5*z*) (for a second of the three anteriolateral approaches), or the second 562 and fourth 566 holes (FIG. 5*aa*) (for a third of the three anteriolateral approaches). And, the left offset repositioner/extractor's shaft 512 can be inserted into the wound from any of its three possible anteriolateral approaches, and the left offset repositioner/extractor's pins 516*a*-*b* can then be placed into the first 560 and second 562 holes (FIG. 5*bb*) (for a first of the three anteriolateral approaches), the first 560 and third 564 holes (FIG. 5*cc*) (for a second of the three anteriolateral approaches), or the second 562 and fourth 566 holes (FIG. 5*dd*) (for a third of the three anteriolateral approaches). It should be noted that the alternate left offset 530 and alternate right offset 540 repositioners/extractors can also fit into the holes of the second hole configuration in the same manner as described here with regard to the left offset 510 and right offset 520 repositioners/extractors.

It should be noted from the illustrations in FIGS. 5*p*-*dd* that the anteriolateral approaches are at a variety of angles relative to the anterior-posterior plane, and further that the illustrated angles are merely exemplary. That is, the invention encompasses additional approach angles, in that such additional approach angles are possible by (as described above) adding or deleting holes, and/or changing the location of holes, and/or changing the spacing between holes (in conjunction with changing the spacing between pins), and/or changing the angle at which the offset repositioner/extractors' pins are placed relative to one another and to the shaft of such repositioner/extractors.

As discussed above, once the pins are established in the two adjacent holes, manipulating the shaft of the repositioner/extractor will reposition the static trial or artificial intervertebral disc in the intervertebral space and/or extract it from the intervertebral space. The use of more than one pin (versus one pin) enables the static trial or artificial intervertebral disc to be rotated in either direction about a longitudinal axis passing through the intervertebral space.

A preferred embodiment of a leveler of the present invention will now be described.

Figure 6A:
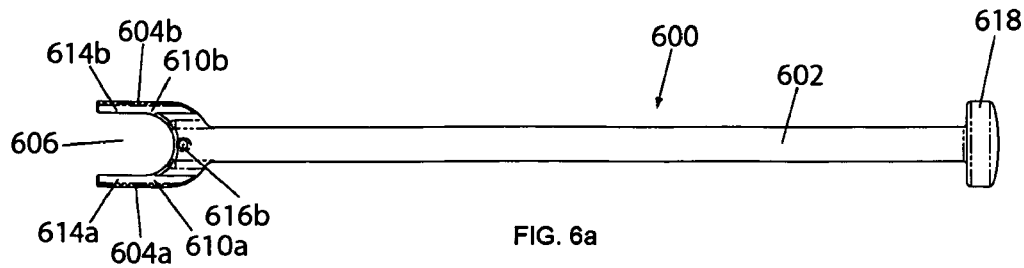
FIGS. 6a-e bottom (FIG. 6a), side (FIG. 6b), front (FIG. 6c), top partial perspective (FIG. 6d), and bottom partial perspective (FIG. 6e) views of a leveler of the present invention.
Figure 6B:
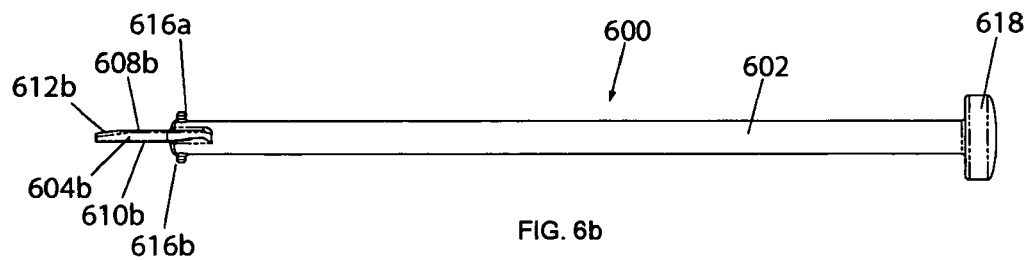
Figure 6C:
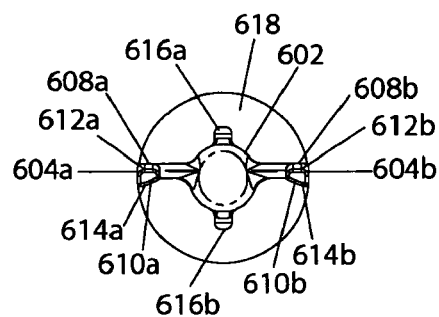
Figure 6D:
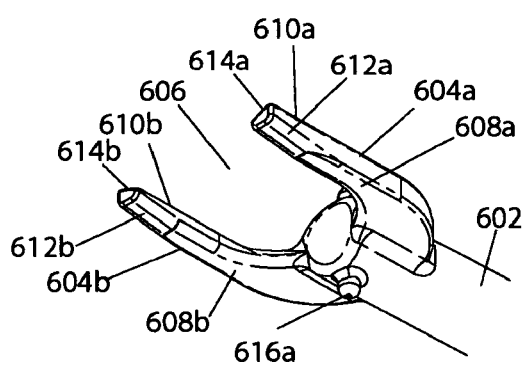
Figure 6E:
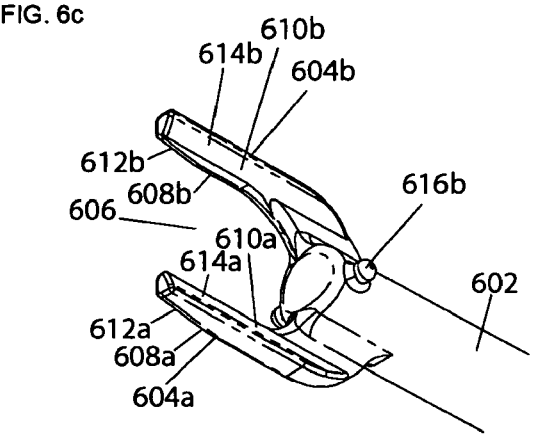

Referring now to FIGS. 6*a*-*e*, a leveler of the present invention is shown in bottom (FIG. 6*a*), side (FIG. 6*b*), front (FIG. 6*c*), top partial perspective (FIG. 6*d*), and bottom partial perspective (FIG. 6*e*) views. More particularly, FIG. 6*d* shows a top perspective view of the distal end of the leveler, and FIG. 6*e* shows a bottom perspective view of the distal end of the leveler.

The leveler is provided primarily for establishing a parallel orientation of the baseplates (relative to one another), and/or securing the purchase of the stabilizing spikes, of an artificial intervertebral disc having features suitable for being manipulated by the leveler. Exemplary suitable artificial intervertebral discs are described in the '160 application with regard to FIGS. 8*a*-*y*, 9*a*-*t*, 10*a*-*t*, 11*a*-*j*, and 12*a*-*o* thereof and by the accompanying descriptions therefor (e.g., embodiments identified as the first, second, third, fourth, and fifth preferred embodiments of the fourth embodiment family, etc.). Regarding the features suitable for being manipulated by the leveler, such features include suitably formed inwardly facing surfaces of the baseplates of the artificial intervertebral disc.

More particularly, the leveler 600 includes a shaft 602 having a forked distal end formed by two opposing tongs 604*a*-*b* that are symmetric to one another about a longitudinal axis of the shaft 602. Each of the tongs 604*a*-*b* has an extent that initially curves laterally outward away from the shaft 602 and from the other tong's extent, to define a central pocket 606 forward of the shaft 602 between the tongs' extents. Each tong's extent then resumes a distal direction to become parallel to the shaft 602 and to the other tong's extent.

Each tong's extent has an upper surface 608*a*-*b* and a lower surface 610*a*-*b*. The upper surface 608*a*-*b* is preferably shaped to conform against the inwardly facing surface of a first (e.g., upper) baseplate of an artificial intervertebral disc, and the lower surface 610*a*-*b* is preferably shaped to conform against the inwardly facing surface of a second (e.g., lower) baseplate of the artificial intervertebral disc, so that insertion of the forked distal end of the leveler 600 between the baseplates, with the central pocket 606 of the distal end avoiding the central portion of the artificial intervertebral disc, and with the upper 608*a*-*b* and lower surfaces 610*a*-*b* so engaging the inwardly facing surfaces of the baseplates, causes the baseplates to be placed in parallel orientation with respect to one another.

More particularly, for example for use with the exemplary artificial intervertebral disc of FIGS. 1*g*-*n*, the upper surface 608*a*-*b* of each extent is flat, except for a tapered section 612*a*-*b* at the distal tip of the extent, which tapered section narrows the tip, and the lower surface 610*a*-*b* of each extent is curved to form opposing concave contours 614*a*-*b* that are cooperatively shaped to conform against the inwardly facing surface of the convex structure of the artificial intervertebral disc.

The preferred use of the leveler 600 is as follows. As discussed above, once the intervertebral space has been prepared and distracted to a dimension that will accept the artificial intervertebral disc to be implanted, the artificial intervertebral disc 160 is engaged at its lower baseplate 168*b* by the inserter/impactor 400 discussed above. During insertion (and, if necessary, impaction) of the artificial intervertebral disc 160 into the intervertebral space, the upper baseplate 168*a* remains free to angulate with respect to the lower baseplate 168*b*, so that the angulation of the baseplates conforms to the angulation of the intervertebral space as the artificial intervertebral disc is being inserted thereinto. Typically, the endplates of the prepared and distracted intervertebral space will be lordotically angled with respect to one another, due to the use of the static trials 100 as described above, which are formed to have a lordotic taper as discussed above. Thus, when the artificial intervertebral disc is inserted into the intervertebral space, its baseplates will be lordotically angled with respect to one another. Once the artificial intervertebral disc 160 is inserted, the inserter/impactor 400 can be disengaged, and the repositioner/extractors 500, 510, 520, 530, 540 discussed above can be applied to the artificial intervertebral disc, if necessary to achieve a more optimal positioning.

Once the positioning is established, the leveler 600 is preferably applied to the artificial intervertebral disc 160. The forked distal end of the leveler 600 is inserted so that the extents 604*a-b* are placed between the inwardly facing surface 164*a* of the upper baseplate 168*a* and the inwardly facing surface 164*b* of the convex structure 162 on the lower baseplate 168*b*, and so that the central pocket 606 of the leveler 600 avoids the ball-and-socket joint of the artificial intervertebral disc 160. If the baseplates are lordotically angled with respect to one another, the tapered sections 612*a-b* of the upper surfaces 608*a-b* of the forked distal end will be approximately parallel to, and will first encounter, the angled inwardly facing surface 164*a* of the upper baseplate 168*a*. At the same time, the concave contours 614*a-b* of the lower surfaces 610*a-b* will accommodate the inwardly facing surface 164*b* of the convex structure 162 on the lower baseplate 168*b*. As the tapered sections 612*a-b* press against the inwardly facing surface 164*a* of the upper baseplate 168*a*, and the concave contours 614*a-b* slip into place against the inwardly facing surface 164*b* of the convex structure 162 on the lower baseplate 168*b*, the tapers 612*a-b* will function as wedges to force the posterior portion of the upper baseplate 168*a* away from the posterior portion of the lower baseplate 168*b*. Accordingly, as the posterior portions are being separated, the stabilizing spikes 188*a-b* on the outwardly facing surfaces 186*a-b* of the baseplates 168*a-b* find or secure their purchase in the hard bone of the outer ring of the vertebral body endplates. When the forked distal end is fully seated (stops 616*a-b* are provided to butt up against the anterior portions of the baseplates 168*a-b* to prevent the forked distal end from being inserted too far), the extents of the tongs 604*a-b* hold the baseplates 168*a-b* parallel to one another, and so that the spikes 188*a-b* are fully engaged in the endplates. The surgeon then slips the leveler 600 out from between the baseplates 168*a-b*, and out from the wound and completes the procedure. A handle 618 is provided at a proximal end of the shaft 602 for pushing, pulling, and otherwise manipulating the leveler 600 as needed.

While there has been described and illustrated specific embodiments of instrumentation, it will be apparent to those skilled in the art that variations and modifications are possible without deviating from the broad spirit and principle of the invention. The invention, therefore, shall not be limited to the specific embodiments discussed herein.

What is claimed is:

1. An apparatus for at least one of distracting an intervertebral space and determining a size of an artificial intervertebral disc to be implanted in the intervertebral space, the apparatus comprising:
    a shaft;
    at least two distal extensions coupled to the shaft, the distal extensions each having a proximal portion, an intermediate portion and a distal portion, the proximal portions and the distal portions of the extensions having a substantially fixed separation from each other and the intermediate portions of the distal extensions capable of moving toward and separating from one another;
    a bifurcated trial having a first trial half of the bifurcated trial coupled by a first pin to a first of the extensions such that the first trial half can pivot with respect to the first of the extensions and having a second trial half of the bifurcated trial fixed to a second of the extensions such that the second trial half cannot pivot with respect to the second of the extensions; and
    a second pin located between the extensions;
    wherein at least one external trial shape of the bifurcated trial approximates at least one external disc shape of a corresponding portion of the artificial intervertebral disc;
    wherein movement of the second pin in a distal direction increases the separation between the intermediate portions of the extensions;
    wherein movement of the second pin in a proximal direction decreases the separation between the intermediate portions of the extensions; and
    wherein varying the separation between the intermediate portions of the extensions varies a separation between the trial halves,
    wherein the first trial halves pivots to place the trial halves in lordosis.

2. The apparatus of claim 1, wherein at least one of the trial halves has an outwardly facing trial surface shaped as a convex dome.

3. The apparatus of claim 1, wherein at least one of the trial halves has a smooth outwardly facing trial surface.

4. The apparatus of claim 1, wherein at least one of the trial halves has an outwardly facing trial surface that approximates a corresponding outwardly facing disc surface of the artificial intervertebral disc.

5. The apparatus of claim 1, further comprising at least one marking, wherein the marking quantifies at least one of the group consisting of a first distance between respective inner surfaces of the trial halves, a second distance between respective outer surfaces of the trial halves, and the size of the artificial intervertebral disc to be implanted in the intervertebral space.

6. The apparatus of claim 5, wherein the marking is located on the shaft.

7. The apparatus of claim 5, wherein at least one of the markings quantifies an artificial intervertebral disc size in a range of 13 mm to 20 mm.

8. The apparatus of claim 1, further comprising at least one flange coupled to a proximal shaft end of the shaft;
    wherein applying pressure to the flange in a distal direction aids insertion of the bifurcated trial into the intervertebral space; and
    wherein applying pressure to the flange in a proximal direction aids extraction of the bifurcated trial from the intervertebral space.

9. The apparatus of claim 1, wherein at least one of the extensions is coupled to a fulcrum of the shaft.

10. The apparatus of claim 1, wherein at least one of the extensions is biased toward the other of the extensions.

11. The apparatus of claim 10, wherein the bias is created by at least one of the group consisting of a spring, a material of at least one of the extensions, a strength of the material, and formation of a fulcrum that is located at a proximal end of at least one of the extensions.

12. The apparatus of claim 1, wherein at least one of the extensions is coupled to the shaft via at least one screw such that the screw limits adjustment of the second pin.

13. The apparatus of claim 1, further comprising an outer shaft portion coupled to the second pin and extending adjacent at least one of the group consisting of a portion of the shaft, and a portion of one of the extensions.

14. The apparatus of claim 13, further comprising a control device coupled to at least one of the outer shaft portion and the second pin; wherein movement of the control device varies the separation of the trial halves.

15. The apparatus of claim 14, wherein the control device is a first control device, and further comprising a second control device, wherein the second control device maintains the trial halves at the separation created by adjustment of the first control device.

16. The apparatus of claim 15, wherein at least one of the control devices is a knob.

17. The apparatus of claim 15, wherein the second control device is threaded to at least a portion of the shaft; and wherein interference between second control device threads of the second control device and shaft threads of the shaft holds the extensions at the separation created by adjustment of the first control device.

18. The apparatus of claim 15, wherein rotation of the second control device increases the separation between the trial halves; and wherein reverse rotation of the second control device decreases the separation between the trial halves.

19. An apparatus for at least one of distracting an intervertebral space and determining a size of an artificial intervertebral disc to be implanted in the intervertebral space, the apparatus comprising:

a shaft;
at least two distal extensions coupled to the shaft;
a bifurcated trial having a first trial half of the bifurcated trial coupled by a first pin to a first of the extensions such that the first trial half can pivot with respect to the first of the extensions and having a second trial half of the bifurcated trial fixed to a second of the extensions such that the second trial half cannot pivot with respect to the second of the extensions; and
a second pin located between the extensions;
wherein at least one external trial shape of the bifurcated trial approximates at least one external disc shape of a corresponding portion of the artificial intervertebral disc;
wherein movement of the second pin in a distal direction increases a separation between the extensions;
wherein movement of the second pin in a proximal direction decreases the separation between the extensions, the increase or decrease of the separation of the extensions causes the first trial half to rotate about the first pin; and
wherein varying the separation between the extensions varies a separation between the trial halves.

* * * * *